US009469584B2

(12) United States Patent
Anton et al.

(10) Patent No.: US 9,469,584 B2
(45) Date of Patent: Oct. 18, 2016

(54) METHOD FOR PRODUCING BUTANOL USING EXTRACTIVE FERMENTATION

(71) Applicant: Butamax Advanced Biofuels LLC, Wilmington, DE (US)

(72) Inventors: Douglas Robert Anton, Wilmington, DE (US); John W. Hallam, Beverley (GB)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 14/772,720

(22) PCT Filed: Mar. 14, 2014

(86) PCT No.: PCT/US2014/029200
§ 371 (c)(1),
(2) Date: Sep. 3, 2015

(87) PCT Pub. No.: WO2014/144684
PCT Pub. Date: Sep. 18, 2014

(65) Prior Publication Data
US 2015/0376096 A1    Dec. 31, 2015

Related U.S. Application Data

(60) Provisional application No. 61/790,401, filed on Mar. 15, 2013.

(51) Int. Cl.
| | | |
|---|---|---|
| *C12P 7/16* | (2006.01) | |
| *C07C 31/12* | (2006.01) | |
| *C07C 29/76* | (2006.01) | |
| *C07C 29/86* | (2006.01) | |

(52) U.S. Cl.
CPC ............. *C07C 29/76* (2013.01); *C07C 29/86* (2013.01); *C12P 7/16* (2013.01); *C07C 31/12* (2013.01); *Y02E 50/10* (2013.01)

(58) Field of Classification Search
CPC ................................. C12P 7/16; C07C 31/12
USPC ................................... 568/913, 840; 435/160
See application file for complete search history.

(56) References Cited

U.S. PATENT DOCUMENTS

| | | | |
|---|---|---|---|
| 4,428,798 A | 1/1984 | Zudkevitch et al. | |
| 4,636,284 A | 1/1987 | English et al. | |
| 4,865,973 A | 9/1989 | Kollerup et al. | |
| 5,374,716 A | 12/1994 | Biermann et al. | |
| 7,851,188 B2 | 12/2010 | Donaldson et al. | |
| 8,373,008 B2 | 2/2013 | Grady et al. | |
| 8,373,009 B2 | 2/2013 | Grady et al. | |
| 8,409,834 B2 | 4/2013 | Burlew et al. | |
| 8,426,173 B2 | 4/2013 | Bramucci et al. | |
| 8,426,174 B2 | 4/2013 | Bramucci et al. | |
| 8,460,439 B2 | 6/2013 | Parten | |
| 8,476,047 B2 | 7/2013 | Burlew et al. | |
| 8,557,540 B2 | 10/2013 | Burlew et al. | |
| 8,563,788 B2 | 10/2013 | Grady et al. | |
| 8,569,552 B2 | 10/2013 | Grady et al. | |
| 8,574,406 B2 | 11/2013 | Grady et al. | |
| 8,617,861 B2 | 12/2013 | Grady et al. | |
| 8,628,643 B2 | 1/2014 | Grady et al. | |
| 8,697,404 B2 | 4/2014 | Anton et al. | |
| 8,759,044 B2 | 6/2014 | DiCosimo et al. | |
| 8,765,425 B2 | 7/2014 | DiCosimo et al. | |
| 8,828,695 B2 | 9/2014 | Grady et al. | |
| 8,865,443 B2 | 10/2014 | Burlew et al. | |
| 8,906,204 B2 | 12/2014 | Xu | |
| 8,968,522 B2 | 3/2015 | Xu et al. | |
| 8,968,523 B2 | 3/2015 | Xu et al. | |
| 8,969,055 B2 | 3/2015 | Grady et al. | |
| 9,156,760 B2 * | 10/2015 | Zaher ...................... C07C 29/86 |
| 2008/0274526 A1 | 11/2008 | Bramucci et al. | |
| 2009/0305370 A1 | 12/2009 | Grady et al. | |
| 2010/0143995 A1 | 6/2010 | Erdner-Tindall et al. | |

(Continued)

FOREIGN PATENT DOCUMENTS

| | | |
|---|---|---|
| GB | 1064317 | 4/1967 |
| JP | 60172290 | 9/1985 |

(Continued)

OTHER PUBLICATIONS

International Preliminary Report on Patentability for corresponding International Application No. PCT/US2014/029200, issued on Sep. 15, 2015.
Adhami, et al., Liquid Extration of Butanol from Dilute Aqueous Solutions Using Soybean-Derived Biodiesel, J. Am. Oil Chem. Soc. 86:1123-1128, 2009.
Jurgens, et al., Butanol Production from Lingocellulosics, Biotechnol. Lett. 34:1415-1434, 2012.
Kim, et al., Extractive Recovery of Products from Fermentation Broths, Biotechnol. Bioprocess Eng. 4:1-11, 1999.

(Continued)

*Primary Examiner* — Elvis O Price

(57) ABSTRACT

The invention relates to a method for producing butanol through microbial fermentation, in which the butanol product is removed by extraction into a water immiscible organic extractant composition during the fermentation. The invention also relates to a method for producing butanol through microbial fermentation, in which the butanol product is removed during the fermentation by extraction into a water-immiscible extractant composition comprising a first solvent having a butanol partition coefficient of at least 3, and a second solvent having a butanol partition coefficient, wherein the butanol partition coefficient of the first solvent is higher than the butanol partition coefficient of the second solvent. Optionally, the first solvent has a higher concentration of hydrogen bonding sites than the second solvent. The invention further relates to a composition including butanol in the water immiscible organic extractant composition described above.

21 Claims, 7 Drawing Sheets

(56) References Cited

U.S. PATENT DOCUMENTS

| | | | |
|---|---|---|---|
| 2011/0097773 A1 | 4/2011 | Grady et al. | |
| 2011/0136193 A1 | 6/2011 | Grady et al. | |
| 2011/0294179 A1 | 12/2011 | Grady et al. | |
| 2011/0312044 A1 | 12/2011 | Anton et al. | |
| 2011/0312053 A1 | 12/2011 | Burlew et al. | |
| 2012/0156738 A1 | 6/2012 | Anton et al. | |
| 2012/0208246 A1 | 8/2012 | Anton et al. | |
| 2012/0323047 A1 | 12/2012 | Dauner et al. | |
| 2013/0164795 A1 | 6/2013 | Lowe et al. | |
| 2013/0217060 A1 | 8/2013 | Bramucci et al. | |
| 2013/0224728 A1 | 8/2013 | Bramucci et al. | |
| 2013/0252297 A1 | 9/2013 | Parten | |
| 2013/0295661 A1 | 11/2013 | Roesch et al. | |
| 2013/0309738 A1 | 11/2013 | Barr et al. | |
| 2014/0018581 A1 | 1/2014 | Grady et al. | |
| 2014/0024064 A1 | 1/2014 | Burlew et al. | |
| 2014/0073021 A1 | 3/2014 | Bazzana et al. | |
| 2014/0073820 A1 | 3/2014 | Bazzana et al. | |
| 2014/0093931 A1 | 4/2014 | Dauner et al. | |
| 2014/0094630 A1 | 4/2014 | Anton et al. | |
| 2014/0099688 A1 | 4/2014 | Grady et al. | |
| 2014/0106419 A1 | 4/2014 | Bazzana et al. | |
| 2014/0142352 A1* | 5/2014 | Dauner .................. | C12P 7/16 568/913 |
| 2014/0162344 A1 | 6/2014 | DiCosimo et al. | |
| 2014/0178529 A1 | 6/2014 | Anton et al. | |
| 2014/0234929 A1 | 8/2014 | Barr et al. | |
| 2014/0256020 A1 | 9/2014 | DiCosimo et al. | |
| 2014/0273127 A1 | 9/2014 | Fuchs et al. | |
| 2014/0273130 A1 | 9/2014 | Anthony et al. | |
| 2014/0303408 A1 | 10/2014 | Zaher et al. | |
| 2014/0311889 A1 | 10/2014 | Zaher et al. | |
| 2014/0363865 A1 | 12/2014 | Burlew et al. | |
| 2015/0010975 A1 | 1/2015 | Burlew et al. | |
| 2015/0010984 A1 | 1/2015 | Bhalla et al. | |
| 2015/0060259 A1 | 3/2015 | Xu | |
| 2015/0211026 A1 | 7/2015 | Bazzana et al. | |
| 2015/0267225 A1 | 9/2015 | Bazzana et al. | |

FOREIGN PATENT DOCUMENTS

| | | |
|---|---|---|
| JP | 61192291 | 8/1986 |
| JP | 62022593 | 1/1987 |
| WO | WO2008/143704 | 11/2008 |
| WO | WO2009/086391 | 7/2009 |

OTHER PUBLICATIONS

Bumbac, et al., Process Modelling and Simulation for 1-Butanol Removing from Fermentation Broth by Extraction with Oleyl Alcohol, Rev. Chim. (Bucharest) 63:727-729, 2012.
Oudshoorn, et al., Short-cut Calculation for Integrated Product Recovery Options in Fermentative Production of Bio-bulk Chemicals, Proc. Biochem. 45:1605-1615, 2010.
Offeman, et al., Extraction of Ethanol with Higher Alcohol Solvents and Their Toxicity to Yeast, Sep. Purif. Technol. 63:444-451, 2008.
Dhamole, et al., Extractive Fermentation with Non-ionic Surfactants to Enhance Butanol Production, Biomass Bioenerg. 40:112-119, 2012.
Atsumi, et al., Non-fermentative pathways for synthesis of branched-chain higher alcohols as biofuels, Nature 451:86-90, 2008.
Bank, et al., Technological aspects of extractive fermentation using aqueous two-phase systems, World J. Microbiol. Biotechnol. 19:337-348, 2003.
Bar, Effect of Interphase Mixing on a Water-Organic Solvent Two-Liquid Phase Microbial. System: Ethanol Fermentation, J. Chem. Tech. Biotechnol. 43:49-62, 1988.
Barba, et al., Hyperazeotropic Ethanol Salted-out by Extractive Distillation. Theoretical Evaluation and Experimenatl Check, Chem. Eng. Sci. 40:2287-2292, 1985.
Barros, et al., Integration of Enzyme Catalysis in an Extractive Fermentation Process, Biocatalysis in Organic Media, Proceedings of International Symposium, Wageningen, The Netherlands, 1986, pp. 185-196.
Bruce, et al., Solvent Selection Strategies for Extractive Biocatalysis, Biotechnol. Prog. 7:116-124, 1991.
Bruce, et al., Extractive Fermentation by Zymomonas mobilis and the Use of Solvent Mixtures, Biotechnol. Lett. 14:71-76, 1992.
Buggert, et al., Prediction of Equilibrum Partitioning of Nonpolar Organic Solutes in Water-Surfactant Systems by UNIFAC and COSMO-RS Models, Chem. Eng. Technol. 29:567-573, 2006.
Carolan, et al., The Effect of Additives and Impurities on the Partition of Ethanol into n-Decanol fom Aqueous Solutions, Dov. Chem. Eng. Mineral Process, 8:551-569, 2000.
Crabbe, et al., Biodiesel production from crude palm oil and evaluation of butanol extraction and fuel properties Proc. Biochem. 37:65-71, 2001.
Daugulis, et al., Continuous Fermentation of High-Strength Glucose Feeds to Ethanol, Biotech. Lett. 16:637-642, 1994.
Daugulis, Integrated Fermentation and Recovery Process, Current Opin. Biotechnol. 5:192-195, 1994.
Davison, et al., Continuous Direct Solvent Extraction of Butanol in a Fermenting Fluidized-Bed Bioreactor with Immobilized Clostridium acetobutylicum, Appl. Biochem. Biotechnol. 39/40:415-426, 1993.
Eckert, et al., Continuous Acetone-Butanol Production with Direct Product Removal, Appl. Microbiol. Biotechnol. 27:221-228, 1987.
Eiteman, et al., In situ Extraction versus the Use of an External Column in Fermentation, Appl. Microbiol. Biotechnol. 30:614,618, 1989.
Evans, et al., Enhancement of Butanol Formaton by Clostridium acetobutylicum in the Presence of Decanol-Oleyl Alcohol Mixed Extractants, Appl. Environ. Microbiol. 54:1662-1667, 1988.
Evans, et al., Response of Clostridium acetobutylicum to the Presence of Mixed Extractants, Appl. Biochem. Biotechnol. 17:175-192, 1988.
Evans, et al., Effects of extractive fermentation on butyric acid production by Clostridium acetobutylicum, Appl. Microbiol. Biotechnol. 32:393,397, 1990.
Ezeji, et al., Butanol Fermentation Research: Upstream and Downstream Manipulations, The Chemical Record 4:305-314, 2004.
Ezeji, et al., Bioproduction of butanol from biomass: from genes to bioreactors, Current Opin. Biotechnol. 18:220-227, 2007.
Ezeji, et al., Achievements and perspectives to overcome the poor solvent resistance in acetone and butanol-producing microorganisms, Appl. Microbiol. Biotechnol. 85:1697-1712, 2010.
Griffith, et al., 1-Butanol Extraction with Vegetable Oil, Fatty-Acid Esters, Developments in Industrial Microbiology, Chapter 76, 25:795-800, 1984.
Grobben, et al., Production of acetone, butanol and ethanol (ABE) from potato wastes: fermentation with integrated membrane extraction, Appl. Microbiol. Biotechnol. 39:494-498, 1993.
Groot, et al., Butanol Recovery from Fermentations by Liquid-Liquid Extraction and Membrance Solvent Extraction, Bioprocess Eng. 5:203-216, 1990.
Groot, et al., Technologies for Butanol Recovery Integrated with Fermentations, Process Biochem, 27:61-75, 1992.
Gyamerah, et al. Productionof Ethanol by Continuous Fermentation and Liquid-Liquid Extraction, J. Chem. Tech. Biotechnol. 66:145-152, 1996.
Honda, et al., Ethanol Fermentation Associated with Solvent Extraction using Immobilized Growing Cells of Saccharomyces cerevislae and its Lactose-Fermentatable Fusant, J. Chem. Eng. Japan 4:268-273, .1986.
Ishii, et al. Production of Butanol by Clostridium acetobutylicum in Extractive Fermentation System, J. Chem. Eng. Japan 18:126-130, 1985.
Ishizaki, et al., Extractive Acetone-Butanol-Ethanol Fermentation Using Methylated Crude Palm Oil as Extractant in Batch Culture of Clostridium saccharoperbutylacetonicum N1-4 (ATCC 13564), J. Biosci. Bioeng. 87:352-356, 1999.
Jeon, et al., Membrane-Assisted Extractive Butanol Fermentation, Ann, N.Y. Acad. Sci, 506:536-542, 1987.

(56) References Cited

OTHER PUBLICATIONS

Jones, et al., Ethanol Production from Lactose by Extractive Fermentation, Biotechnol. Lett. 15:871-876, 1993.
Malinowski, Liquid-liquid and Vapour-liquid Behavior of Oleyl Alcohol Applied to Extractive Fermentation Processing, Can. J. Chem. Eng. 71:431-436, 1993.
Malinowski, et al., Salt Effects in Extraction of Ethanol, 1-Butanol and Acetone from Aqueous Solutions, AIChE J. 40:1459-1465, 1994.
Malinowski, Two-phase partitioning bioreactors in fermentation technoiogy, Biotechnol. Adv. 19:525-538, 2001.
Matsumura, et al., Application of Solvent Extraction to Ethanol Fermentation, Appl. Microbiol. Biotecnol. 20:371-377, 1984.
Matsumura, et al., Energy saving effect of pervaporation using oleyl alcohol liquid membrane in butanol purification, Bioprocess Eng. 3:93-100, 1988.
Minier, et al,, Ethanol Production by Extractive Fermentation, Biotechnol. Bioeng. 24:1565-1579, 1982.
Mitchell, et al., Ethanol from Dilute Aqueous Solution by Liquid-Liquid Extraction, Biotechnol. Bioeng. 30:348-351, 1987.
Munson, et al., Factors Influencing Solvent Selection for Extraction of Ethanol from Aqueous Solutions, Ind. Eng. Chem. Process Des. Dev. 23:115-121, 1984.
Offeman, et al,, Extraction of Ethanol with Higher Carboxylic Acids Solvents and their Toxicity to yeast, Sep. Purif. Technol. 72:180-185, 2010.
Oliviera, et al., Production and Extractive Biocatalysis of Ethanol Using Microencapsulated Yeast Cells and Lipase System, J. Chem. Technol. Biotechnol. 52:219-225, 1991.
Oliviera, et al., lmprovement of alcoholic fermentations by simultaneous extraction and enzymatic esterification of ethanol, J. Molecular Catalysis B: Enzymatic 5:29-33, 1998.
Oudshoorn, et al., Assessment of Options for Selective 1-Butanol Recovery from Aqueous Solution, Ind. Eng. Chem. Res. 48:7325-7336, 2009.
Pfennig, et al., Influence of Electrolytes on Liquid-Liquid Extraction, Ind. Eng. Chem. Res. 37:3180-3188, 1988.
Qureshi, et al., Continuous Production of Acetone-Butanol-Ethanol Using Immobilized Cells of Clostridium acetobutylicum and Integration with Product Removal by Liquid-Liquid Extraction, J. Ferment. Bioeng. 80:185-189, 1995.
Ramey, Production of Butyric Acid and Butanol from Biomass, Final Report, Dept. of Energy, Contract No. DE-F-G02-00ER86106, 2004.
Roffler, Extractive Fermentation-Lactic Acid and Acetone/Butanol Production, Dissertation, Univ. of California, Berkeley, 1986.
Roffler. et al., Extractive Fermenaton of Acetone and Butanol: Process Design and Economic Evaluation, Biotechnol. Progress 3:131-140, 1987.
Roffler, et al., In-situ Recovery of Butanol during Fermentation, Bioprocess Eng. 2:1-12, 1987.
Roffler, et al., In situ Extractive Fermentation of Acetone and Butanol, Biotechnol. Bioeng. 31:135-143, 1988.
Roffler, et al., Extractive Bioconversions with Nonaqueous Solvents, Extractive Bioconversions, Marcel Dekker, Inc. N.Y., 1990, pp. 133-172.
Schugerl, Integrated Processing of Biotechnology Products, Biotechnol. Adv. 18:581-599, 2000.
Taya, et al., Monitoring and Control for Extractive Fermentation of Clostridium acetobutylicum, J. Ferment. technol. 63:181-187, 1985.
Vane, Separation Technologies for the Recovery and Dehydration of Alcohols from Fermentation Broths, Biofuels. Bioprod. Bioref. 2:553-588, 2008.
Wang, et al., Enhanced Alcohol Production Through On-Line Extraction, Third Symposium on Biotechnology in Energy Production and Conservation, Biotechnol. Bioeng. Symp. 11:555-565, 1981.
Wayman, et al., Production of Acetone-Butanol by Extractive Fermentation Using Dibutylphthalate as Extractant, J. Ferment. Technol. 65:295-300, 1987.
Weilnhammer, et al., Continuous Fermentation with Product Recovery by in-situ Extraction, Chem. Eng, Technol. 17:365-373, 1994.
International Search Report for corresponding International Application No. PCT/US2014/029200, mailed Jun. 24, 2014.

\* cited by examiner

US 9,469,584 B2

METHOD FOR PRODUCING BUTANOL USING EXTRACTIVE FERMENTATION

CROSS-REFERENCE

This application claims priority to U.S. Provisional Patent Application No. 61/790,401, filed on 15 Mar. 2013, entitled Method for Production of Butanol Using Extractive Fermentation, which is hereby incorporated by reference in its entirety. Additionally, this application incorporates by reference in their entireties U.S. Provisional Patent Application No. 61/788,213, filed on 15 Mar. 2013, entitled Method for Production of Butanol Using Extractive Fermentation, and U.S. Provisional Patent Application No. 61/790,828, filed on 15 Mar. 2013, entitled Method for Production of Butanol Using Extractive Fermentation.

FIELD OF THE INVENTION

The invention relates to the field of biofuels. More specifically, the invention relates to a method for producing butanol through microbial fermentation, in which the butanol product is removed by extraction into a water immiscible organic extractant during the fermentation. The invention also relates to a method for producing butanol through microbial fermentation, in which the butanol product is removed during the fermentation by extraction into a water-immiscible extractant composition which comprises a first solvent and a second solvent.

BACKGROUND OF THE INVENTION

Butanol is an important industrial chemical, with a variety of applications, such as use as a fuel additive, as a feedstock chemical in the plastics industry, and as a food grade extractant in the food and flavor industry. Each year 10 to 12 billion pounds of butanol are produced by petrochemical means and the need for this chemical will likely increase.

Several chemical synthetic methods are known; however, these methods of producing butanol use starting materials derived from petrochemicals and are generally expensive and are not environmentally friendly. Several methods of producing butanol by fermentation are also known, for example the ABE process which is the fermentive process producing a mixture of acetone, 1-butanol and ethanol. Acetone-butanol-ethanol (ABE) fermentation by *Clostridium acetobutylicum* is one of the oldest known industrial fermentations; as is also the pathways and genes responsible for the production of these solvents. Production of 1-butanol by the ABE process is limited by the toxic effect of the 1-butanol on *Clostridium acetobutylicum*. In situ extractive fermentation methods using specific organic extractants which are nontoxic to the bacterium have been reported to enhance the production of 1-butanol by fermentation using *Clostridium acetobutylicum* (Roffler et al., Biotechnol. Bioeng. 31:135-143, 1988; Roffler et al., Bioprocess Engineering 2:1-12, 1987; and Evans et al., Appl. Environ. Microbiol. 54:1662-1667, 1988).

In contrast to the native *Clostridium acetobutylicum* described above, recombinant microbial production hosts expressing 1-butanol, 2-butanol, and isobutanol biosynthetic pathways have also been described. These recombinant hosts have the potential of producing butanol in higher yields compared to the ABE process because they do not produce byproducts such as acetone and ethanol. With these recombinant hosts, the biological production of butanol appears to be limited by the butanol toxicity thresholds of the host microorganism used in the fermentation. U.S. Patent Application Publication Nos. 2009/0305370 and 2011/0097773, each of which is incorporated herein by reference in its entirety, discloses a method of making butanol from at least one fermentable carbon source that overcomes the issues of toxicity resulting in an increase in the effective titer, the effective rate, and the effective yield of butanol production by fermentation utilizing a recombinant microbial host wherein the butanol is extracted into specific organic extractants during fermentation.

Improved methods for producing and recovering butanol from a fermentation medium are continually sought. Lower cost processes and improvements to process operability are also desired. Identification of improved extractants for use with fermentation media, such as extractants exhibiting higher partition coefficients, lower viscosity, lower density, commercially useful boiling points, and sufficient microbial biocompatibility, is a continual need.

SUMMARY OF THE INVENTION

Provided herein are methods for recovering butanol from a fermentation medium. The methods comprise (a) providing a fermentation medium comprising butanol, water, and a recombinant microorganism comprising a butanol biosynthetic pathway, wherein the recombinant microorganism produces butanol; (b) contacting the fermentation medium with a water immiscible organic extractant composition comprising a first solvent, having a butanol partition coefficient of at least about 3, and a second solvent having a butanol partition coefficient, to form a butanol-containing organic phase and an aqueous phase, wherein the butanol partition coefficient of the first solvent is higher than the butanol partition coefficient of the second solvent; and (c) recovering the butanol from the butanol-containing organic phase.

In some embodiments, the first solvent is 2-ethyl-1-hexanol, $(R)_3P=O$, wherein each R may independently be hexyl or octyl, tributyl phosphate, bis(2-ethyl hexyl) phosphate, 3,7-dimethyl-1-octanol, 3,5,5-trimethyl-1-hexanol, nonyl phenol, farnesol, or mixtures thereof. In some embodiments, the second solvent is oleyl alcohol, 2-butyl-1-octanol, 2-hexyl-1-decanol, castor oil fatty acid methyl esters, sunflower oil fatty acids, bis-(2-ethylhexyl) adipate, petroleum ether, corn oil, corn oil fatty acids, or mixtures thereof.

In some embodiments, the first solvent has a butanol partition coefficient of at least about 3.5, 4, 4.5, 5, 5.5, 6, 6.5, 7, 7.5, or 8. In other embodiments, the first solvent has a higher concentration of hydrogen bonding sites per molecule than the second solvent.

In some embodiments, the second solvent is oleyl alcohol, 2-butyl-1-octanol, 2-hexyl-1-decanol, castor oil fatty acid methyl ester, soy oil fatty acids (SOFA), bis-(2-ethylhexyl) adipate, petroleum ether, corn oil, corn oil fatty acids (COFA), or mixtures thereof.

In certain embodiments, the methods for recovering butanol from a fermentation medium comprise (a) providing a fermentation medium comprising butanol, water, and a recombinant microorganism comprising a butanol biosynthetic pathway, wherein the recombinant microorganism produces butanol; (b) contacting the fermentation medium with a water immiscible organic extractant composition comprising a first solvent, wherein the first solvent is 2-ethyl-1-hexanol, $(R)_3P=O$, wherein each R may independently be hexyl or octyl, tributyl phosphate, bis(2-ethyl hexyl) phosphate, 3,7-dimethyl-1-octanol, 3,5,5-trimethyl- 1-hexanol, nonyl phenol, farnesol, or mixtures thereof, and a second solvent, wherein the second solvent is oleyl alcohol, 2-butyl-1-octanol, 2-hexyl-1-decanol, castor oil fatty acid methyl ester, soy oil fatty acids (SOFA), bis-(2-ethylhexyl) adipate, petroleum ether, corn oil, corn oil fatty acids (COFA), or mixtures thereof, to form a butanol-containing organic phase and an aqueous phase; and (c) recovering the butanol from the butanol-containing organic phase.

In some embodiments, the contacting comprises contacting the fermentation medium via a co-current or counter-current stream of the organic extractant composition.

In some embodiments, the contacting of the organic extractant composition with the fermentation medium occurs in the fermentor. In other embodiments, the contacting of the organic extractant composition with the fermentation medium occurs outside the fermentor. In some embodiments, the butanol is recovered after transferring a portion of the fermentation medium from the fermentor to a vessel, wherein the contacting of the organic extractant composition with the fermentation medium occurs in the vessel.

In some embodiments, the recovered butanol has an effective titer from about 20 g per liter to about 50 g per liter of the fermentation medium. In some embodiments, the recovered butanol has an effective titer from about 22 g per liter to about 50 g per liter. In some embodiments, the recovered butanol has an effective titer from about 25 g per liter to about 50 g per liter. In embodiments, the recovered butanol has an effective titer of at least 25 g, at least 30 g, at least 35 g, at least 37 g, at least 40 g, or at least 45 g per liter of the fermentation medium.

Also provided is a composition, comprising butanol in a water immiscible organic extractant composition, wherein said organic extractant composition comprises (a) a first solvent having a butanol partition coefficient of at least about 3; and (b) a second solvent having a butanol partition coefficient, wherein the butanol partition coefficient of the first solvent is higher than the butanol partition coefficient of the second solvent.

In some embodiments, the first solvent of the organic extractant composition is 2-ethyl-1-hexanol, $(R)_3P=O$, wherein each R may independently be hexyl or octyl, tributyl phosphate, bis(2-ethyl hexyl) phosphate, 3,7-dimethyl-1-octanol, 3,5,5-trimethyl-1-hexanol, nonyl phenol, farnesol, or mixtures thereof, and the second solvent is oleyl alcohol, 2-butyl-1-octanol, 2-hexyl-1-decanol, castor oil fatty acid methyl ester, soy oil fatty acids (SOFA), bis-(2-ethylhexyl) adipate, petroleum ether, corn oil, corn oil fatty acids (COFA), or mixtures thereof.

In embodiments, the first solvent of the organic extractant composition has a butanol partition coefficient of at least about 3.5, 4, 4.5, 5, 5.5, 6, 6.5, 7, 7.5, or 8. In other embodiments, the first solvent has a higher concentration of hydrogen bonding sites per molecule than the second solvent.

Another embodiment is a composition comprising butanol in a water immiscible organic extractant composition, wherein said organic extractant composition comprises (a) a first solvent, wherein the first solvent is 2-ethyl-1-hexanol, $(R)_3P=O$, wherein each R may independently be hexyl or octyl, tributyl phosphate, bis(2-ethyl hexyl) phosphate, 3,7-dimethyl-1-octanol, 3,5,5-trimethyl-1-hexanol, nonyl phenol, farnesol, or mixtures thereof; and (b) a second solvent, wherein the second solvent is oleyl alcohol, 2-butyl-1-octanol, 2-hexyl-1-decanol, castor oil fatty acid methyl ester, soy oil fatty acids (SOFA), bis-(2-ethylhexyl) adipate, petroleum ether, corn oil, corn oil fatty acids (COFA), or mixtures thereof.

In some embodiments, the butanol is 1-butanol. In embodiments, the butanol is 2-butanol. In some embodiments, the butanol is isobutanol.

DETAILED DESCRIPTION OF THE INVENTION

Figure 1:
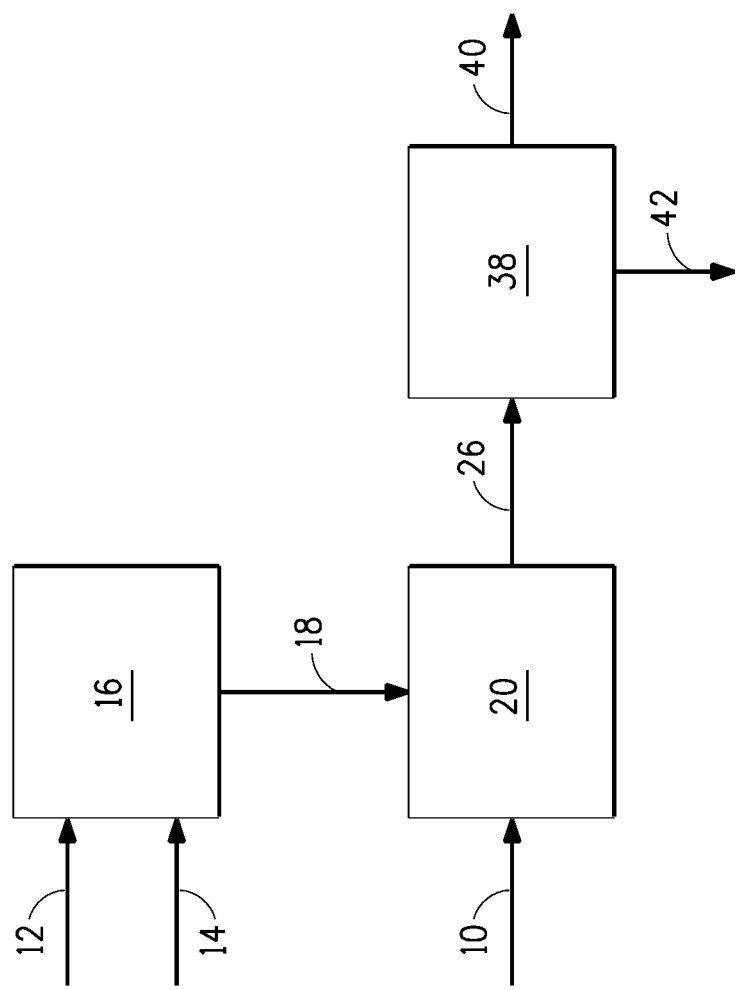
FIG. 1 schematically illustrates one embodiment of the methods of the invention, in which the first solvent and the second solvent of which the extractant composition is comprised are combined in a vessel prior to contacting the fermentation medium with the extractant in a fermentation vessel.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further define this invention, the following terms, abbreviations and definitions are provided.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. §2111.03.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the claims as presented or as later amended and supplemented, or in the specification.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, or within 5% of the reported numerical value.

The term "butanol biosynthetic pathway" as used herein refers to the enzymatic pathway to produce 1-butanol, 2-butanol, or isobutanol.

The term "1-butanol biosynthetic pathway" refers to an enzymatic pathway to produce 1-butanol. A "1-butanol biosynthetic pathway" can refer to an enzyme pathway to produce 1-butanol from acetyl-coenzyme A (acetyl-CoA). For example, 1-butanol biosynthetic pathways are disclosed in U.S. Patent Application Publication No. 2008/0182308 and International Publication No. WO 2007/041269, which are herein incorporated by reference in their entireties.

The term "2-butanol biosynthetic pathway" refers to an enzymatic pathway to produce 2-butanol. A "2-butanol biosynthetic pathway" can refer to an enzyme pathway to produce 2-butanol from pyruvate. For example, 2-butanol biosynthetic pathways are disclosed in U.S. Pat. No. 8,206,970, U.S. Patent Application Publication No. 2007/0292927, International Publication Nos. WO 2007/130518 and WO 2007/130521, which are herein incorporated by reference in their entireties.

The term "isobutanol biosynthetic pathway" refers to an enzymatic pathway to produce isobutanol. An "isobutanol biosynthetic pathway" can refer to an enzyme pathway to produce isobutanol from pyruvate. For example, isobutanol biosynthetic pathways are disclosed in U.S. Pat. No. 7,851,188, U.S. Application Publication No. 2007/0092957, and International Publication No. WO 2007/050671, which are herein incorporated by reference in their entireties. From time to time "isobutanol biosynthetic pathway" is used synonymously with "isobutanol production pathway."

The term "butanol" as used herein refers to the butanol isomers 1-butanol (1-BuOH), 2-butanol (2-BuOH), tert-butanol (t-BuOH), and/or isobutanol (iBuOH or i-BuOH, also known as 2-methyl-1-propanol), either individually or as mixtures thereof. From time to time, as used herein the terms "biobutanol" and "bio-produced butanol" may be used synonymously with "butanol."

Uses for butanol can include, but are not limited to, fuels (e.g., biofuels), a fuel additive, an alcohol used for the production of esters that can be used as diesel or biodiesel fuel, as a chemical in the plastics industry, an ingredient in formulated products such as cosmetics, and a chemical intermediate. Butanol may also be used as a solvent for paints, coatings, varnishes, resins, gums, dyes, fats, waxes, resins, shellac, rubbers, and alkaloids.

As used herein, the term "bio-produced" means that the molecule (e.g., butanol) is produced from a renewable source (e.g., the molecule can be produced during a fermentation process from a renewable feedstock). Thus, for example, bio-produced isobutanol can be isobutanol produced by a fermentation process from a renewable feedstock. Molecules produced from a renewable source can further be defined by the $^{14}C/^{12}C$ isotope ratio. A $^{14}C/^{12}C$ isotope ratio in range of from 1:0 to greater than 0:1 indicates a bio-produced molecule, whereas a ratio of 0:1 indicates that the molecule is fossil derived.

"Product alcohol" as used herein, refers to any alcohol that can be produced by a microorganism in a fermentation process that utilizes biomass as a source of fermentable carbon substrate. Product alcohols include, but are not limited to, $C_1$ to $C_8$ alkyl alcohols, and mixtures thereof. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, pentanol, and mixtures thereof. Likewise $C_2$ to $C_8$ alkyl alcohols include, but are not limited to, ethanol, propanol, butanol, and pentanol. "Alcohol" is also used herein with reference to a product alcohol.

A recombinant host cell comprising an "engineered alcohol production pathway" (such as an engineered butanol or isobutanol production pathway) refers to a host cell containing a modified pathway that produces alcohol in a manner different than that normally present in the host cell. Such differences include production of an alcohol not typically produced by the host cell, or increased or more efficient production.

The term "heterologous biosynthetic pathway" as used herein refers to an enzyme pathway to produce a product in which at least one of the enzymes is not endogenous to the host cell containing the biosynthetic pathway.

The term "butanologen" as used herein refers to a microorganism capable of producing butanol. The term "isobutanologen" as used herein refers to a microorganism capable of producing isobutanol.

The term "ethanologen" as used herein refers to a microorganism capable of producing ethanol.

The term "extractant" as used herein refers to one or more organic solvents which can be used to extract a product alcohol. From time to time as used herein, the term "extractant" may be used synonymously with "solvent."

The term "effective isobutanol productivity" as used herein refers to the total amount in grams of isobutanol produced per gram of cells.

The term "effective titer" as used herein, refers to the total amount of a particular alcohol (e.g., butanol) produced by fermentation per liter of fermentation medium. The total amount of butanol includes: (i) the amount of butanol in the fermentation medium; (ii) the amount of butanol recovered from the organic extractant; and (iii) the amount of butanol recovered from the gas phase, if gas stripping is used.

The term "effective rate" as used herein, refers to the total amount of butanol produced by fermentation per liter of fermentation medium per hour of fermentation.

The term "effective yield" as used herein, refers to the amount of butanol produced per unit of fermentable carbon substrate consumed by the biocatalyst.

The term "separation" as used herein is synonymous with "recovery" and refers to removing a chemical compound from an initial mixture to obtain the compound in greater purity or at a higher concentration than the purity or concentration of the compound in the initial mixture.

The term "In Situ Product Removal" (ISPR) as used herein refers to the selective removal of a fermentation product from a biological process such as fermentation to control the product concentration as the product is produced.

The term "aqueous phase," as used herein, refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction, and the terms "solvent-poor phase" may be used synonymously with "aqueous phase" and "fermentation broth.".

The term "organic phase," as used herein, refers to the non-aqueous phase of a biphasic mixture obtained by contacting a fermentation broth with a water-immiscible organic extractant. From time to time, as used herein the terms "solvent-rich phase" may be used synonymously with "organic phase."

The term "aqueous phase titer" as used herein, refers to the concentration of product alcohol (e.g., butanol) in the fermentation broth.

The term "water-immiscible" as used herein refers to a chemical component such as an extractant or a solvent, which is incapable of mixing with an aqueous solution such as a fermentation broth, in such a manner as to form one liquid phase.

The term "biphasic fermentation medium" as used herein refers to a two-phase growth medium comprising a fermentation medium (i.e., an aqueous phase) and a suitable amount of a water-immiscible organic extractant.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof. Non-limiting examples of carbon substrates are provided herein and include, but are not limited to, monosaccharides, disaccharides, oligosaccharides, polysaccharides, ethanol, lactate, succinate, glycerol, carbon dioxide, methanol, glucose, fructose, lactose, sucrose, xylose, arabinose, dextrose, cellulose, methane, amino acids, or mixtures thereof.

"Fermentation broth" as used herein means the mixture of water, sugars (fermentable carbon sources), dissolved solids (if present), microorganisms producing alcohol, product alcohol and all other constituents of the material in which product alcohol is being made by the reaction of sugars to alcohol, water and carbon dioxide ($CO_2$) by the microorganisms present. From time to time, as used herein the term "fermentation medium" and "fermented mixture" can be used synonymously with "fermentation broth."

As used herein a "fermentor" refers to any container, containers, or apparatus that are used to ferment a substrate. A fermentor can contain a fermentation medium and microorganism capable of fermentation. The term "fermentation vessel" refers to the vessel in which the fermentation reaction is carried out whereby alcohol such as butanol is made from sugars. "Fermentor" can be used herein interchangeable with "fermentation vessel."

The term "fermentation product" includes any desired product of interest, including, but not limited to 1-butanol, 2-butanol, isobutanol, etc.

The term "sugar" as used herein, refers to oligosaccharides, disaccharides, monosaccharides, and/or mixtures thereof. The term "saccharide" also includes carbohydrates including starches, dextrans, glycogens, cellulose, pentosans, as well as sugars.

The term "fermentable sugar" as used herein, refers to one or more sugars capable of being metabolized by the microorganisms disclosed herein for the production of fermentative alcohol.

The term "undissolved solids" as used herein, means non-fermentable portions of feedstock, for example, germ, fiber, and gluten. For example, the non-fermentable portions of feedstock include the portion of feedstock that remains as solids and can absorb liquid from the fermentation broth.

"Biomass" as used herein refers to a natural product containing a hydrolysable starch that provides a fermentable sugar, including any cellulosic or lignocellulosic material and materials comprising cellulose, and optionally further comprising hemicellulose, lignin, starch, oligosaccharides, disaccharides, and/or monosaccharides. Biomass can also comprise additional components, such as protein and/or lipids. Biomass can be derived from a single source, or biomass can comprise a mixture derived from more than one source. For example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood, and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

"Feedstock" as used herein means a product containing a fermentable carbon source. Suitable feedstock include, but are not limited to, rye, wheat, corn, corn mash, cane, cane mash, sugar cane, barley, cellulosic material, lignocellulosic material, and mixtures thereof.

The term "aerobic conditions" as used herein means growth conditions in the presence of oxygen.

The term "microaerobic conditions" as used herein means growth conditions with low levels of oxygen (i.e., below normal atmospheric oxygen levels).

The term "anaerobic conditions" as used herein means growth conditions in the absence of oxygen.

The term "minimal media" as used herein refers to growth media that contain the minimum nutrients possible for growth, generally without the presence of amino acids. A minimal medium typically contains a fermentable carbon source and various salts, which may vary among microorganisms and growing conditions; these salts generally provide essential elements such as magnesium, nitrogen, phosphorous, and sulfur to allow the microorganism to synthesize proteins and nucleic acids.

The term "defined media" as used herein refers to growth media that have known quantities of all ingredients, e.g., a defined carbon source and nitrogen source, and trace elements and vitamins required by the microorganism.

The term "biocompatibility" as used herein refers to the measure of the ability of a microorganism to utilize glucose in the presence of an extractant. A biocompatible extractant permits the microorganism to utilize glucose. A non-biocompatible (i.e., a biotoxic) extractant does not permit the microorganism to utilize glucose, for example, at a rate greater than about 25% of the rate when the extractant is not present.

The term "toxicity" of solvent as used herein refers to the percentage of butanol-producing microorganisms killed after exposure to the solvent for a prolonged time, for example 24 hours.

The term "free volume" as used herein refers to the proportion of a volume of bulk solvent that is not occupied by solvent molecules.

The term "fatty acid" as used herein, refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein, refers to an alcohol having an aliphatic chain of $C_4$ to $C_{22}$ carbon atoms, which is either saturated or unsaturated.

The term "fatty aldehyde" as used herein, refers to an aldehyde having an aliphatic chain of $C_4$ to $C_{22}$ carbon atoms, which is either saturated or unsaturated.

The term "fatty amide" as used herein, refers to an amide having a long, aliphatic chain of $C_4$ to $C_{22}$ carbon atoms, which is either saturated or unsaturated.

The term "fatty ester" as used herein, refers to an ester having a long aliphatic chain of $C_4$ to $C_{22}$ carbon atoms, which is either saturated or unsaturated.

The term "carboxylic acid" as used herein, refers to any organic compound with the general chemical formula —COOH in which a carbon atom is bonded to an oxygen atom by a double bond to make a carbonyl group (—C=O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

The term "alkane" as used herein refers to a saturated hydrocarbon.

"Portion" as used herein, includes a part of a whole or the whole. For example, a portion of fermentation broth includes a part of the fermentation broth as well as the whole (or all) the fermentation broth.

"Partition coefficient" or "$K_d$" refers to the ratio of the concentration of a compound in the two phases of a mixture of two immiscible solvents at equilibrium. A partition coefficient is a measure of the differential solubility of a compound between two immiscible solvents. Partition coefficient, as used herein, is synonymous with the term distribution coefficient.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene can comprise regulatory sequences and coding sequences that are derived from different sources, or regulatory sequences and coding sequences derived from the same source, but arranged in a manner different than that found in nature. "Endogenous gene" refers to a native gene in its natural location in the genome of a microorganism. A "foreign" gene refers to a gene not normally found in the host microorganism, but that is introduced into the host microorganism by gene transfer. Foreign genes can comprise native genes inserted into a non-native microorganism, or chimeric genes. A "transgene" is a gene that has been introduced into the genome by a transformation procedure.

As used herein, "native" refers to the form of a polynucleotide, gene, or polypeptide as found in nature with its own regulatory sequences, if present.

As used herein the term "coding sequence" or "coding region" refers to a DNA sequence that encodes for a specific amino acid sequence.

As used herein, "endogenous" refers to the native form of a polynucleotide, gene or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism transcribed and translated from a native polynucleotide or gene in its natural location in the genome of an organism.

The term "heterologous" when used in reference to a polynucleotide, a gene, or a polypeptide refers to a polynucleotide, gene, or polypeptide not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene can be introduced into the host organism by, e.g., gene transfer. A heterologous gene can include a native coding region with non-native regulatory regions that is reintroduced into the native host. For example, a heterologous gene can include a native coding region that is a portion of a chimeric gene including non-native regulatory regions that is reintroduced into the native host. "Heterologous polypeptide" includes a native polypeptide that is reintroduced into the source organism in a form that is different from the corresponding native polypeptide. A "heterologous" polypeptide or polynucleotide can also include an engineered polypeptide or polynucleotide that comprises a difference from the "native" polypeptide or polynucleotide, e.g., a point mutation within the endogenous polynucleotide can result in the production of a "heterologous" polypeptide. As used herein a "chimeric gene," a "foreign gene," and a "transgene," can all be examples of "heterologous" genes.

A "transgene" is a gene that has been introduced into the genome by a transformation procedure.

Microorganisms

Microbial hosts for butanol production can be selected from bacteria, cyanobacteria, filamentous fungi and yeasts. The microbial host used should be tolerant to the butanol product produced, so that the yield is not limited by toxicity of the product to the host. The selection of a microbial host for butanol production is described in detail below.

Microbes that are metabolically active at high titer levels of butanol are not well known in the art. Although butanol-tolerant mutants have been isolated from solventogenic Clostridia, little information is available concerning the butanol tolerance of other potentially useful bacterial strains. Most of the studies on the comparison of alcohol tolerance in bacteria suggest that butanol is more toxic than ethanol (de Cavalho et al., Microsc. Res. Tech. 64:215-22 (2004) and Kabelitz et al., FEMS Microbiol. Lett. 220:223-227 (2003)). Tomas et al. (J. Bacteriol. 186:2006-2018 (2004)) report that the yield of 1-butanol during fermentation in *Clostridium acetobutylicum* can be limited by butanol toxicity. The primary effect of 1-butanol on *Clostridium acetobutylicum* is disruption of membrane functions (Hermann et al., Appl. Environ. Microbiol. 50:1238-1243 (1985)).

The microbial hosts selected for the production of butanol should be tolerant to butanol and should be able to convert carbohydrates to butanol using the introduced biosynthetic pathway as described below. The criteria for selection of suitable microbial hosts include the following: intrinsic tolerance to butanol, high rate of carbohydrate utilization, availability of genetic tools for gene manipulation, and the ability to generate stable chromosomal alterations.

Suitable host strains with a tolerance for butanol can be identified by screening based on the intrinsic tolerance of the strain. The intrinsic tolerance of microbes to butanol can be measured by determining the concentration of butanol that is responsible for 50% inhibition of the growth rate (IC50) when grown in a minimal medium. The IC50 values can be determined using methods known in the art. For example, the microbes of interest can be grown in the presence of various amounts of butanol and the growth rate monitored by measuring the optical density at 600 nanometers. The doubling time can be calculated from the logarithmic part of the growth curve and used as a measure of the growth rate. The concentration of butanol that produces 50% inhibition of growth can be determined from a graph of the percent inhibition of growth versus the butanol concentration. In one embodiment, the host strain has an IC50 for butanol of greater than about 0.5%. In another embodiment, the host strain has an IC50 for butanol that is greater than about 1.5%. In yet another embodiment, the host strain has an IC50 for butanol that is greater than about 2.5%.

The microbial host for butanol production should also utilize glucose and/or other carbohydrates at a high rate. Most microbes are capable of utilizing carbohydrates. However, certain environmental microbes cannot efficiently use carbohydrates, and therefore would not be suitable hosts.

The ability to genetically modify the host is essential for the production of any recombinant microorganism. Modes of gene transfer technology that can be used include, for example, electroporation, conjugation, transduction or natural transformation. A broad range of host conjugative plasmids and drug resistance markers are available. The cloning vectors used with an organism are tailored to the host organism based on the nature of antibiotic resistance markers that can function in that host.

The microbial host also can be manipulated in order to inactivate competing pathways for carbon flow by inactivating various genes. This requires the availability of either transposons or chromosomal integration vectors to direct inactivation. Additionally, production hosts that are amenable to chemical mutagenesis can undergo improvements in intrinsic butanol tolerance through chemical mutagenesis and mutant screening.

Based on the criteria described above, suitable microbial hosts for the production of butanol include, but are not limited to, members of the genera, *Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Pichia, Candida, Hansenula* and *Saccharomyces*. In some embodiments, the host can be: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Pediococcus pentosaceus, Pediococcus acidilactici, Bacillus subtilis* or *Saccharomyces cerevisiae*.

Recombinant Microorganisms

While not wishing to be bound by theory, it is believed that the processes described herein are useful in conjunction with any alcohol producing microorganism, particularly recombinant microorganisms which produce alcohol.

Recombinant microorganisms which produce alcohol are also known in the art (e.g., Ohta et al., Appl. Environ. Microbiol. 57:893-900 (1991); Underwood et al., Appl. Environ. Microbiol. 68:1071-81 (2002); Shen and Liao, Metab. Eng. 10:312-20 (2008); Hahnai et al., Appl. Environ. Microbiol. 73:7814-8 (2007); U.S. Pat. No. 5,514,583; U.S. Pat. No. 5,712,133; International Publication No. WO 1995/028476; Feldmann et al., Appl. Microbiol. Biotechnol. 38:354-61 (1992); Zhang et al., Science 267:240-3 (1995); U.S. Patent Publication No. 2007/0031918A1; U.S. Pat. No. 7,223,575;

U.S. Pat. No. 7,741,119; U.S. Patent Publication No. 2009/0203099A1; U.S. Patent Publication No. 2009/0246846A1; and International Publication No. WO 2010/075241, which are herein incorporated by reference).

For example, the metabolic pathways of microorganisms may be genetically modified to produce butanol. These pathways may also be modified to reduce or eliminate undesired metabolites, and thereby improve yield of the product alcohol. The production of butanol by a microorganism is disclosed, for example, in U.S. Pat. Nos. 7,851,188; 7,993,889; 8,178,328, 8,206,970; U.S. Patent Application Publication Nos. 2007/0292927; 2008/0182308; 2008/0274525; 2009/0305363; 2009/0305370; 2011/0250610; 2011/0313206; 2011/0111472; 2012/0258873; and U.S. patent application Ser. No. 13/428,585, the entire contents of each are herein incorporated by reference. In some embodiments, microorganisms comprise a butanol biosynthetic pathway or a biosynthetic pathway for a butanol isomer such as 1-butanol, 2-butanol, or isobutanol. In some embodiments, the biosynthetic pathway converts pyruvate to a fermentative product. In some embodiments, the biosynthetic pathway converts pyruvate as well as amino acids to a fermentative product. In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism.

In some embodiments, the microorganism may be bacteria, cyanobacteria, filamentous fungi, or yeasts. Suitable microorganisms capable of producing product alcohol (e.g., butanol) via a biosynthetic pathway include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma,* or *Saccharomyces*. In one embodiment, recombinant microorganisms may be selected from the group consisting of *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis, Candida sonorensis, Candida methanosorbosa, Kluyveromyces lactis, Kluyveromyces marxianus, Kluveromyces thermotolerans, Issatchenkia orientalis, Debaryomyces hansenii,* and *Saccharomyces cerevisiae*. In one embodiment, the genetically modified microorganism is yeast. In one embodiment, the genetically modified microorganism is a crabtree-positive yeast selected from *Saccharomyces, Zygosaccharomyces, Schizosaccharomyces, Dekkera, Torulopsis, Brettanomyces,* and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Zygosaccharomyces rouxii, Zygosaccharomyces bailli,* and *Candida glabrata*.

In some embodiments, the host cell is *Saccharomyces cerevisiae*. *Saccharomyces cerevisiae* are known in the art and are available from a variety of sources including, but not limited to, American Type Culture Collection (Rockville, Md.), Centralbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

In some embodiments, the microorganism may be immobilized or encapsulated. For example, the microorganism may be immobilized or encapsulated using alginate, calcium alginate, or polyacrylamide gels, or through the induction of biofilm formation onto a variety of high surface area support matrices such as diatomite, celite, diatomaceous earth, silica gels, plastics, or resins. In some embodiments, ISPR may be used in combination with immobilized or encapsulated microorganisms. This combination may improve productivity such as specific volumetric productivity, metabolic rate, product alcohol yields, tolerance to product alcohol. In addition, immobilization and encapsulation may minimize the effects of the process conditions such as shearing on the microorganisms.

Biosynthetic pathways for the production of isobutanol that may be used include those as described by Donaldson et al. in U.S. Pat. No. 7,851,188; U.S. Pat. No. 7,993,388; and International Publication No. WO 2007/050671, which are incorporated herein by reference. In one embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by acetohydroxy acid reductoisomerase;

c) the 2,3-dihydroxyisovalerate from step b) to α-ketoisovalerate, which may be catalyzed, for example, by acetohydroxy acid dehydratase;

d) the α-ketoisovalerate from step c) to isobutyraldehyde, which may be catalyzed, for example, by a branched-chain α-keto acid decarboxylase; and, e) the isobutyraldehyde from step d) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by ketol-acid reductoisomerase;

c) the 2,3-dihydroxyisovalerate from step b) to α-ketoisovalerate, which may be catalyzed, for example, by dihydroxyacid dehydratase;

d) the α-ketoisovalerate from step c) to valine, which may be catalyzed, for example, by transaminase or valine dehydrogenase;

e) the valine from step d) to isobutylamine, which may be catalyzed, for example, by valine decarboxylase;

f) the isobutylamine from step e) to isobutyraldehyde, which may be catalyzed by, for example, omega transaminase; and, g) the isobutyraldehyde from step f) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by acetohydroxy acid reductoisomerase;

c) the 2,3-dihydroxyisovalerate from step b) to α-ketoisovalerate, which may be catalyzed, for example, by acetohydroxy acid dehydratase;

d) the α-ketoisovalerate from step c) to isobutyryl-CoA, which may be catalyzed, for example, by branched-chain keto acid dehydrogenase;

e) the isobutyryl-CoA from step d) to isobutyraldehyde, which may be catalyzed, for example, by acylating aldehyde dehydrogenase; and, f) the isobutyraldehyde from step e) to isobutanol, which may be catalyzed, for example, by a branched-chain alcohol dehydrogenase.

Biosynthetic pathways for the production of 1-butanol that may be used include those described in U.S. Patent Application Publication No. 2008/0182308 and WO2007/041269, which are incorporated herein by reference. In one embodiment, the 1-butanol biosynthetic pathway comprises the following substrate to product conversions:

a) acetyl-CoA to acetoacetyl-CoA, which may be catalyzed, for example, by acetyl-CoA acetyltransferase;

b) the acetoacetyl-CoA from step a) to 3-hydroxybutyryl-CoA, which may be catalyzed, for example, by 3-hydroxybutyryl-CoA dehydrogenase;

c) the 3-hydroxybutyryl-CoA from step b) to crotonyl-CoA, which may be catalyzed, for example, by crotonase;

d) the crotonyl-CoA from step c) to butyryl-CoA, which may be catalyzed, for example, by butyryl-CoA dehydrogenase;

e) the butyryl-CoA from step d) to butyraldehyde, which may be catalyzed, for example, by butyraldehyde dehydrogenase; and, f) the butyraldehyde from step e) to 1-butanol, which may be catalyzed, for example, by butanol dehydrogenase.

Biosynthetic pathways for the production of 2-butanol that may be used include those described by Donaldson et al. in U.S. Pat. No. 8,206,970; U.S. Patent Application Publication Nos. 2007/0292927 and 2009/0155870; International Publication Nos. WO 2007/130518 and WO 2007/130521, all of which are incorporated herein by reference. In one embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetonin aminase;

d) the 3-amino-2-butanol from step c) to 3-amino-2-butanol phosphate, which may be catalyzed, for example, by aminobutanol kinase;

e) the 3-amino-2-butanol phosphate from step d) to 2-butanone, which may be catalyzed, for example, by aminobutanol phosphate phosphorylase; and, f) the 2-butanone from step e) to 2-butanol, which may be catalyzed, for example, by butanol dehydrogenase.

In another embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin to 2,3-butanediol from step b), which may be catalyzed, for example, by butanediol dehydrogenase;

d) the 2,3-butanediol from step c) to 2-butanone, which may be catalyzed, for example, by dial dehydratase; and, e) the 2-butanone from step d) to 2-butanol, which may be catalyzed, for example, by butanol dehydrogenase.

Biosynthetic pathways for the production of 2-butanone that may be used include those described in U.S. Pat. No. 8,206,970 and U.S. Patent Application Publication Nos. 2007/0292927 and 2009/0155870, which are incorporated herein by reference. In one embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetonin aminase;

d) the 3-amino-2-butanol from step c) to 3-amino-2-butanol phosphate, which may be catalyzed, for example, by aminobutanol kinase; and, e) the 3-amino-2-butanol phosphate from step d) to 2-butanone, which may be catalyzed, for example, by aminobutanol phosphate phosphorylase.

In another embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin which may be catalyzed, for example, by acetolactate decarboxylase;

c) the acetoin from step b) to 2,3-butanediol, which may be catalyzed, for example, by butanediol dehydrogenase;

d) the 2,3-butanediol from step c) to 2-butanone, which may be catalyzed, for example, by diol dehydratase.

The terms "acetohydroxyacid synthase," "acetolactate synthase," and "acetolactate synthetase" (abbreviated "ALS") are used interchangeably herein to refer to an enzyme that catalyzes the conversion of pyruvate to acetolactate and $CO_2$. Example acetolactate synthases are known by the EC number 2.2.1.6 (Enzyme Nomenclature 1992, Academic Press, San Diego). These enzymes are available from a number of sources, including, but not limited to, *Bacillus subtilis* (GenBank Nos: CAB07802.1, Z99122, NCBI (National Center for Biotechnology Information) amino acid sequence, NCBI nucleotide sequence, respectively), CAB 15618, *Klebsiella pneumoniae* (GenBank Nos: AAA25079, M73842), and *Lactococcus lactis* (GenBank Nos: AAA25161, L16975)

The term "ketol-acid reductoisomerase" ("KARI"), "acetohydroxy acid isomeroreductase," and "acetohydroxy acid reductoisomerase" will be used interchangeably and refer to enzymes capable of catalyzing the reaction of (S)-acetolactate to 2,3-dihydroxyisovalerate. Example KARI enzymes may be classified as EC number EC 1.1.1.86 (Enzyme Nomenclature 1992, Academic Press, San Diego), and are available from a vast array of microorganisms, including, but not limited to, *Escherichia coli* (GenBank Nos: NP_418222, NC_000913), *Saccharomyces cerevisiae*

(GenBank Nos: NP_013459, NC_001144), *Methanococcus maripaludis* (GenBank Nos: CAF30210, BX957220), *Bacillus subtilis* (GenBank Nos: CAB 14789, Z99118), and *Anaerostipes caccae*. Ketol-acid reductoisomerase (KARI) enzymes are described in U.S. Pat. Nos. 7,910,342 and 8,129,162; U.S. Patent Application Publication Nos. 2008/0261230, 2009/0163376, 2010/0197519, PCT Application Publication No. WO/2011/041415, PCT Application Publication No. WO2012/129555; and U.S. Provisional Application No. 61/705,977, filed on Sep. 26, 2012, all of which are incorporated herein by reference. Examples of KARIs disclosed therein are those from *Lactococcus lactis, Vibrio cholera, Pseudomonas aeruginosa* PAO1, and *Pseudomonas fluorescens* PF5 mutants. In some embodiments, the KARI utilizes NADH. In some embodiments, the KARI utilizes NADPH. In some embodiments, the KARI utilizes NADH or NADPH.

The term "acetohydroxy acid dehydratase" and "dihydroxyacid dehydratase" ("DHAD") refers to an enzyme that catalyzes the conversion of 2,3-dihydroxyisovalerate to α-ketoisovalerate. Example acetohydroxy acid dehydratases are known by the EC number 4.2.1.9. Such enzymes are available from a vast array of microorganisms, including, but not limited to, *E. coli* (GenBank Nos: YP_026248, NC000913), *Saccharomyces cerevisiae* (GenBank Nos: NP_012550, NC 001142), *M. maripaludis* (GenBank Nos: CAF29874, BX957219), *B. subtilis* (GenBank Nos: CAB14105, Z99115), *L. lactis*, and *N. crassa*. U.S. Patent Application Publication No. 2010/0081154, U.S. Pat. No. 7,851,188, and U.S. Pat. No. 8,241,878, which are incorporated herein by reference in their entireties, describe dihydroxyacid dehydratases (DHADs), including a DHAD from *Streptococcus mutans* and variants thereof The term "branched-chain α-keto acid decarboxylase," "α-ketoacid decarboxylase," "α-ketoisovalerate decarboxylase," or "2-ketoisovalerate decarboxylase" ("KIVD") refers to an enzyme that catalyzes the conversion of α-ketoisovalerate to isobutyraldehyde and $CO_2$. Example branched-chain α-keto acid decarboxylases are known by the EC number 4.1.1.72 and are available from a number of sources, including, but not limited to, *Lactococcus lactis* (GenBank Nos: AAS49166, AY548760; CAG34226, AJ746364), *Salmonella typhimurium* (GenBank Nos: NP_461346, NC_003197), *Clostridium acetobutylicum* (GenBank Nos: NP_149189, NC_001988), *M. caseolyticus*, and *L. grayi*.

The term "branched-chain alcohol dehydrogenase" ("ADH") refers to an enzyme that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Alcohol dehydrogenases may be NADPH dependent or NADH dependent. Such enzymes are available from a number of sources, including, but not limited to, *S. cerevisiae* (GenBank Nos: NP_010656, NC_001136, NP_014051, NC_001145), *E. coli* (GenBank Nos: NP_417484, NC_000913), *C. acetobutylicum* (GenBank Nos: NP_349892, NC_003030; NP_349891, NC_003030). U.S. Patent Application Publication No. 2009/0269823 describes SadB, an alcohol dehydrogenase (ADH) from *Achromobacter xylosoxidans*. Alcohol dehydrogenases can also include horse liver ADH and *Beijerinkia indica* ADH, as described by U.S. Patent Application Publication No. 2011/0269199, which is incorporated herein by reference in its entirety.

The term "butanol dehydrogenase" refers to a polypeptide (or polypeptides) having an enzyme activity that catalyzes the conversion of isobutyraldehyde to isobutanol or the conversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* (GenBank Nos: CAD36475, AJ491307). The NADP dependent enzymes are known as EC 1.1.1.2 and are available, for example, from *Pyrococcus furiosus* (GenBank Nos: AAC25556, AF013169). Additionally, a butanol dehydrogenase is available from *Escherichia coli* (GenBank Nos: NP_417484, NC_000913) and a cyclohexanol dehydrogenase is available from *Acinetobacter* sp. (GenBank Nos: AAG10026, AF282240). The term "butanol dehydrogenase" also refers to an enzyme that catalyzes the conversion of butyraldehyde to 1-butanol, using either NADH or NADPH as cofactor. Butanol dehydrogenases are available from, for example, *C. acetobutylicum* (GenBank NOs: NP_149325, NC_001988; note: this enzyme possesses both aldehyde and alcohol dehydrogenase activity); NP_349891, NC_003030; and NP_349892, NC_003030) and *E. coli* (GenBank NOs: NP_417-484, NC_000913).

The term "branched-chain keto acid dehydrogenase" refers to an enzyme that catalyzes the conversion of α-ketoisovalerate to isobutyryl-CoA (isobutyryl-coenzyme A), typically using $NAD^+$ (nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms, including, but not limited to, *B. subtilis* (GenBank Nos: CAB14336, Z99116; CAB14335, Z99116; CAB14334, Z99116; and CAB14337, Z99116) and *Pseudomonas putida* (GenBank Nos: AAA65614, M57613; AAA65615, M57613; AAA65617, M57613; and AAA65618, M57613).

The term "acylating aldehyde dehydrogenase" refers to an enzyme that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources, including, but not limited to, *Clostridium beijerinckii* (GenBank Nos: AAD31841, AF157306), *C. acetobutylicum* (GenBank Nos: NP_149325, NC_001988; NP_149199, NC_001988), *P. putida* (GenBank Nos: AAA89106, U13232), and *Thermus thermophilus* (GenBank Nos: YP_145486, NC_006461).

The term "transaminase" refers to an enzyme that catalyzes the conversion of α-ketoisovalerate to L-valine, using either alanine or glutamate as an amine donor. Example transaminases are known by the EC numbers 2.6.1.42 and 2.6.1.66. Such enzymes are available from a number of sources. Examples of sources for alanine-dependent enzymes include, but are not limited to, *E. coli* (GenBank Nos: YP_026231, NC_000913) and *Bacillus licheniformis* (GenBank Nos: YP_093743, NC_006322). Examples of sources for glutamate-dependent enzymes include, but are not limited to, *E. coli* (GenBank Nos: YP_026247, NC_000913), *Saccharomyces cerevisiae* (GenBank Nos: NP_012682, NC_001142) and *Methanobacterium thermoautotrophicum* (GenBank Nos: NP_276546, NC_000916).

The term "valine dehydrogenase" refers to an enzyme that catalyzes the conversion of α-ketoisovalerate to L-valine, typically using NAD(P)H as an electron donor and ammonia as an amine donor. Example valine dehydrogenases are known by the EC numbers 1.4.1.8 and 1.4.1.9 and such enzymes are available from a number of sources, including, but not limited to, *Streptomyces coelicolor* (GenBank Nos: NP_628270, NC_003888) and *B. subtilis* (GenBank Nos: CAB14339, Z99116).

The term "valine decarboxylase" refers to an enzyme that catalyzes the conversion of L-valine to isobutylamine and $CO_2$. Example valine decarboxylases are known by the EC number 4.1.1.14. Such enzymes are found in *Streptomyces*, such as for example, *Streptomyces viridifaciens* (GenBank Nos: AAN10242, AY116644).

The term "omega transaminase" refers to an enzyme that catalyzes the conversion of isobutylamine to isobutyraldehyde using a suitable amino acid as an amine donor. Example omega transaminases are known by the EC number 2.6.1.18 and are available from a number of sources, including, but not limited to, *Alcaligenes denitrificans* (AAP92672, AY330220), *Ralstonia eutropha* (GenBank Nos: YP_294474, NC_007347), *Shewanella oneidensis* (GenBank Nos: NP_719046, NC_004347), and *P. putida* (GenBank Nos: AAN66223, AE016776).

The term "acetyl-CoA acetyltransferase" refers to an enzyme that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1, NC_003030; NP_149242, NC_001988, *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Example hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314, NC_003030), *B. subtilis* (GenBank NOs: AAB09614, U29084), *Ralstonia eutropha* (GenBank NOs: YP_294481, NC_007347), and *Alcaligenes eutrophus* (GenBank NOs: AAA21973, J04987).

The term "crotonase" refers to an enzyme that catalyzes the conversion of 3-hydroxybutyryl-CoA to crotonyl-CoA and $H_2O$. Example crotonases may have a substrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *E. coli* (GenBank NOs: NP_415911, NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase" refers to an enzyme that catalyzes the conversion of crotonyl-CoA to butyryl-CoA. Example butyryl-CoA dehydrogenases may be NADH-dependent, NADPH-dependent, or flavin-dependent and may be classified as E.C. 1.3.1.44, E.C. 1.3.1.38, and E.C. 1.3.99.2, respectively. Butyryl-CoA dehydrogenases are available from a number of sources, for example, *C. acetobutylicum* (GenBank NOs: NP_347102, NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841, AF157306) and *C. acetobutylicum* (GenBank NOs: NP_149325, NC_001988).

The term "isobutyryl-CoA mutase" refers to an enzyme that catalyzes the conversion of butyryl-CoA to isobutyryl-CoA. This enzyme uses coenzyme $B_{12}$ as cofactor. Example isobutyryl-CoA mutases are known by the EC number 5.4.99.13. These enzymes are found in a number of *Streptomyces*, including, but not limited to, *Streptomyces cinnamonensis* (GenBank Nos: AAC08713, U67612; CAB59633, AJ246005), *S. coelicolor* (GenBank Nos: CAB70645, AL939123; CAB92663, AL939121), and *Streptomyces avermitilis* (GenBank Nos: NP_824008, NC_003155; NP_824637, NC_003155).

The term "acetolactate decarboxylase" refers to a polypeptide (or polypeptides) having an enzyme activity that catalyzes the conversion of alpha-acetolactate to acetoin. Example acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (GenBank Nos: AAU43774, AY722056).

The term "acetoin aminase" or "acetoin transaminase" refers to a polypeptide (or polypeptides) having an enzyme activity that catalyzes the conversion of acetoin to 3-amino-2-butanol. Acetoin aminase may utilize the cofactor pyridoxal 5'-phosphate or NADH (reduced nicotinamide adenine dinucleotide) or NADPH (reduced nicotinamide adenine dinucleotide phosphate). The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH dependent acetoin aminase, also known as amino alcohol dehydrogenase, is described by Ito, et al. (U.S. Pat. No. 6,432,688). An example of a pyridoxal-dependent acetoin aminase is the amine:pyruvate aminotransferase (also called amine:pyruvate transaminase) described by Shin and Kim (*J. Org. Chem.* 67:2848-2853, 2002).

The term "acetoin kinase" refers to a polypeptide (or polypeptides) having an enzyme activity that catalyzes the conversion of acetoin to phosphoacetoin. Acetoin kinase may utilize ATP (adenosine triphosphate) or phosphoenolpyruvate as the phosphate donor in the reaction. Enzymes that catalyze the analogous reaction on the similar substrate dihydroxyacetone, for example, include enzymes known as EC 2.7.1.29 (Garcia-Alles, et al., *Biochemistry* 43:13037-13046, 2004).

The term "acetoin phosphate aminase" refers to a polypeptide (or polypeptides) having an enzyme activity that catalyzes the conversion of phosphoacetoin to 3-amino-2-butanol 0-phosphate. Acetoin phosphate aminase may use the cofactor pyridoxal 5'-phosphate, NADH or NADPH. The resulting product may have (R) or (S) stereochemistry at the 3-position. The pyridoxal phosphate-dependent enzyme may use an amino acid such as alanine or glutamate. The NADH and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta, et al., *Appl. Environ. Microbial.* 67:4999-5009, 2001).

The term "aminobutanol phosphate phospholyase," also called "amino alcohol O-phosphate lyase," refers to a polypeptide (or polypeptides) having an enzyme activity that catalyzes the conversion of 3-amino-2-butanol 0-phosphate to 2-butanone. Amino butanol phosphate phospho-lyase may utilize the cofactor pyridoxal 5'-phosphate. There are reports of enzymes that catalyze the analogous reaction on the similar substrate 1-amino-2-propanol phosphate (Jones, et al., Biochem J. 134:167-182, 1973). U.S. Patent Application Publication No. 2007/0259410 describes an aminobutanol phosphate phospho-lyase from the organism *Erwinia carotovora*.

The term "aminobutanol kinase" refers to a polypeptide (or polypeptides) having an enzyme activity that catalyzes the conversion of 3-amino-2-butanol to 3-amino-2-butanol 0-phosphate. Amino butanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones, et al., supra). U.S. Patent Application Publication No. 2009/0155870 describes, in Example 14, an amino alcohol kinase of *Erwinia carotovora* subsp. *Atroseptica*.

The term "butanediol dehydrogenase" also known as "acetoin reductase" refers to a polypeptide (or polypeptides) having an enzyme activity that catalyzes the conversion of acetoin to 2,3-butanediol. Butanedial dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085, D86412). (R)-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase," also known as "dial dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (also known as coenzyme Bw or vitamin $B_{12}$; although vitamin B12 may refer also to other forms of cobalamin that are not coenzyme B12). Adenosyl cobalamin-dependent enzymes are known as EC 4.2.1.28 and are available, for example, from *Klebsiella oxytoca* (GenBank Nos: AA08099 (alpha subunit), D45071; BAA08100 (beta subunit), D45071; and BBA08101 (gamma subunit), D45071 (Note all three subunits are required for activity), and *Klebsiella pneumonia* (GenBank Nos: AAC98384 (alpha subunit), AF102064; GenBank Nos: AAC98385 (beta subunit), AF102064, GenBank Nos: AAC98386 (gamma subunit), AF102064). Other suitable dial dehydratases include, but are not limited to, B12-dependent dial dehydratases available from *Salmonella typhimurium* (GenBank Nos: AAB84102 (large subunit), AF026270; GenBank Nos: AAB84103 (medium subunit), AF026270; GenBank Nos: AAB84104 (small subunit), AF026270); and *Lactobacillus collinoides* (GenBank Nos: CAC82541 (large subunit), AJ297723; GenBank Nos: CAC82542 (medium subunit); AJ297723; GenBank Nos: CAD01091 (small subunit), AJ297723); and enzymes from *Lactobacillus brevis* (particularly strains CNRZ 734 and CNRZ 735, Speranza, et al., *J. Agric. Food Chem.* 45:3476-3480, 1997), and nucleotide sequences that encode the corresponding enzymes. Methods of diol dehydratase gene isolation are well known in the art (e.g., U.S. Pat. No. 5,686,276).

The term "pyruvate decarboxylase" refers to an enzyme that catalyzes the decarboxylation of pyruvic acid to acetaldehyde and carbon dioxide. Pyruvate dehydrogenases are known by the EC number 4.1.1.1. These enzymes are found in a number of yeast, including *Saccharomyces cerevisiae* (GenBank Nos: CAA97575, CAA97705, CAA97091).

It will be appreciated that host cells comprising an isobutanol biosynthetic pathway as provided herein may further comprise one or more additional modifications. U.S. Patent Application Publication No. 2009/0305363 (incorporated by reference) discloses increased conversion of pyruvate to acetolactate by engineering yeast for expression of a cytosol-localized acetolactate synthase and substantial elimination of pyruvate decarboxylase activity. In some embodiments, the host cells comprise modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Application Publication No. 2009/0305363 (incorporated herein by reference), modifications to a host cell that provide for increased carbon flux through an Entner-Doudoroff Pathway or reducing equivalents balance as described in U.S. Patent Application Publication No. 2010/0120105 (incorporated herein by reference). Other modifications include integration of at least one polynucleotide encoding a polypeptide that catalyzes a step in a pyruvate-utilizing biosynthetic pathway.

Other modifications include at least one deletion, mutation, and/or substitution in an endogenous polynucleotide encoding a polypeptide having acetolactate reductase activity. As used herein, "acetolactate reductase activity" refers to the activity of any polypeptide having the ability to catalyze the conversion of acetolactate to DHMB. Such polypeptides can be determined by methods well known in the art and disclosed herein. As used herein, "DHMB" refers to 2,3-dihydroxy-2-methyl butyrate. DHMB includes "fast DHMB," which has the 2S, 3S configuration, and "slow DHMB," which has the 2S, 3R configurate. See Kaneko et al., *Phytochemistry* 39: 115-120 (1995), which is herein incorporated by reference in its entirety and refers to fast DHMB as anglyceric acid and slow DHMB as tiglyceric acid. In embodiments, the polypeptide having acetolactate reductase activity is YMR226C of *Saccharomyces cerevisiae* or a homolog thereof.

Additional modifications include a deletion, mutation, and/or substitution in an endogenous polynucleotide encoding a polypeptide having aldehyde dehydrogenase and/or aldehyde oxidase activity. As used herein, "aldehyde dehydrogenase activity" refers to any polypeptide having a biological function of an aldehyde dehydrogenase. Such polypeptides include a polypeptide that catalyzes the oxidation (dehydrogenation) of aldehydes. Such polypeptides include a polypeptide that catalyzes the conversion of isobutyraldehyde to isobutyric acid. Such polypeptides also include a polypeptide that corresponds to Enzyme Commission Numbers EC 1.2.1.3, EC 1.2.1.4 or EC 1.2.1.5. Such polypeptides can be determined by methods well known in the art and disclosed herein. As used herein, "aldehyde oxidase activity" refers to any polypeptide having a biological function of an aldehyde oxidase. Such polypeptides include a polypeptide that catalyzes production of carboxylic acids from aldehydes. Such polypeptides include a polypeptide that catalyzes the conversion of isobutyraldehyde to isobutyric acid. Such polypeptides also include a polypeptide that corresponds to Enzyme Commission Number EC 1.2.3.1. Such polypeptides can be determined by methods well known in the art and disclosed herein. In some embodiments, the polypeptide having aldehyde dehydrogenase activity is ALD6 from *Saccharomyces cerevisiae* or a homolog thereof A genetic modification which has the effect of reducing glucose repression wherein the yeast production host cell is pdc-is described in U.S. Patent Application Publication No. 2011/0124060, incorporated herein by reference. In some embodiments, the pyruvate decarboxylase that is deleted or down-regulated is selected from the group consisting of: PDC1, PDC5, PDC6, and combinations thereof. In some embodiments, the pyruvate decarboxylase is selected from PDC1 pyruvate decarboxylase from *Saccharomyces cerevisiae*, PDC5 pyruvate decarboxylase from *Saccharomyces cerevisiae*, PDC6 pyruvate decarboxylase from *Saccharomyces cerevisiae*, pyruvate decarboxylase from *Candida glabrata*, PDC1 pyruvate decarboxylase from *Pichia stipites*, PDC2 pyruvate decarboxylase from *Pichia stipites*, pyruvate decarboxylase from *Kluveromyces lactis*, pyruvate decarboxylase from *Yarrowia lipolytica*, pyruvate decarboxylase from *Schizosaccharomyces pombe*, and pyruvate decarboxylase from *Zygosaccharomyces rouxii*. In some embodiments, host cells contain a deletion or down-regulation of a polynucleotide encoding a polypeptide that catalyzes the conversion of glyceraldehyde-3-phosphate to glycerate 1,3, bisphosphate. In some embodiments, the enzyme that catalyzes this reaction is glyceraldehyde-3-phosphate dehydrogenase.

WIPO publication number WO 2001/103300 discloses recombinant host cells comprising (a) at least one heterologous polynucleotide encoding a polypeptide having dihydroxy-acid dehydratase activity; and (b)(i) at least one deletion, mutation, and/or substitution in an endogenous gene encoding a polypeptide affecting Fe—S cluster biosynthesis; and/or (ii) at least one heterologous polynucleotide encoding a polypeptide affecting Fe—S cluster biosynthesis. In embodiments, the polypeptide affecting Fe—S cluster biosynthesis is encoded by AFT1, AFT2, FRA2, GRX3, or CCC1. In embodiments, the polypeptide affecting Fe—S cluster biosynthesis is constitutive mutant AFT1 L99A, AFT1 L102A, AFT1 C291F, or AFT1 C293F.

Additionally, host cells may comprise heterologous polynucleotides encoding a polypeptide with phosphoketolase activity and/or a heterologous polynucleotide encoding a polypeptide with phosphotransacetylase activity.

In some embodiments, any particular nucleic acid molecule or polypeptide may be at least 80%, 85%, 90%, 95%, 96%, 97%, 98%, or 99% identical to a nucleotide sequence or polypeptide sequence described herein. The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Standard recombinant DNA and molecular cloning techniques are well known in the art and are described by Sambrook, et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis) and by Ausubel, et al. (Ausubel, et al., *Current Protocols in Molecular Biology*, pub. by Greene Publishing Assoc. and Wiley-Interscience, 1987). Examples of methods to construct microorganisms that comprise a butanol biosynthetic pathway are disclosed, for example, in U.S. Pat. No. 7,851,188, and U.S. Patent Application Publication Nos. 2007/0092957; 2007/0259410; 2007/0292927; 2008/0182308; 2008/0274525; 2009/0155870; 2009/0305363; and 2009/0305370, the entire contents of each are herein incorporated by reference.

Organic Extractants

A product alcohol may be recovered from fermentation broth using a number of methods including liquid-liquid extraction. In some embodiments of the processes and systems described herein, an extractant may be used to recover product alcohol from fermentation broth. Extractants used herein may be have, for example, one or more of the following properties and/or characteristics: (i) biocompatible with the microorganisms, (ii) immiscible with the fermentation medium, (iii) a high partition coefficient ($K_d$) for the extraction of product alcohol, (iv) a low partition coefficient for the extraction of nutrients and other side products, (v) a low spreading coefficient, (vi) a high interfacial tension with water, (vii) low viscosity ($\mu$), (viii) high selectivity for product alcohol as compared to, for example, water, (ix) low density ($\rho$) relative to the fermentation medium, (x) boiling point suitable for downstream processing of the extractant and product alcohol, (xi) melting point lower than ambient temperature, (xii) minimal solubility in solids, (xiii) a low tendency to form emulsions with the fermentation medium, (xiv) stability over the fermentation process, (xv) low cost, (xvi) commercial availability, and (xvii) nonhazardous.

In some embodiments, the extractant may be selected based upon certain properties and/or characteristics as described above. For example, viscosity of the extractant can influence the mass transfer properties of the system, for example, the efficiency with which the product alcohol may be extracted from the aqueous phase to the extractant phase (i.e., organic phase). The density of the extractant can affect phase separation. In some embodiments, the extractant may be liquid at the temperatures of the fermentation process. In some embodiments, selectivity refers to the relative amounts of product alcohol to water taken up by the extractant. The boiling point can affect the cost and method of product alcohol recovery. For example, in the case where butanol is recovered from the extractant phase by distillation, the boiling point of the extractant should be sufficiently low as to enable separation of butanol while minimizing any thermal degradation or side reactions of the extractant, or the need for vacuum in the distillation process.

The extractant can be biocompatible with the microorganism, that is, nontoxic to the microorganism or toxic only to such an extent that the microorganism is impaired to an acceptable level. In some embodiments, biocompatible refers to the measure of the ability of a microorganism to utilize fermentable carbon sources in the presence of an extractant. The extent of biocompatibility of an extractant may be determined, for example, by the glucose utilization rate of the microorganism in the presence of the extractant and product alcohol. In some embodiments, a non-biocompatible extractant refers to an extractant that interferes with the ability of a microorganism to utilize fermentable carbon sources. For example, a non-biocompatible extractant does not permit the microorganism to utilize glucose at a rate greater than about 25%, greater than about 30%, greater than about 35%, greater than about 40%, greater than about 45%, or greater than about 50% of the rate when the extractant is not present.

One skilled in the art may select an extractant to maximize the desired properties and/or characteristics as described above and to optimize recovery of a product alcohol. One of skill in the art can also appreciate that it may be advantageous to use a mixture of extractants. For example, extractant mixtures may be used to increase the partition coefficient for the product alcohol. Additionally, extractant mixtures may be used to adjust and optimize physical characteristics of the extractant, such as the density, boiling point, and viscosity. For example, the appropriate combination may provide an extractant which has a sufficient partition coefficient for the product alcohol, sufficient biocompatibility to enable its economical use for removing product alcohol from a fermentative broth, and sufficient selectivity to enable the selective removal of the product alcohol over, for example, water.

In some embodiments, the extractant compositions can achieve one or more of the qualities mentioned above by mixing two or more solvents. In some embodiments, suitable organic extractant compositions for use in the methods disclosed herein are organic extractant compositions comprising a first solvent having a butanol partition coefficient of at least about 3, and a second solvent having a butanol partition coefficient, wherein the butanol partition coefficient of the first solvent is higher than the butanol partition coefficient of the second solvent, to form a butanol-containing organic phase and an aqueous phase. In some embodiments, the first solvent also has a higher concentration of hydrogen bonding sites per unit volume than the second solvent. In some embodiments, the first solvent also has greater free volume than the second solvent. In some embodiments, the first solvent has a higher concentration of hydrogen bonding sites and greater free volume than the second solvent. The resulting organic extractant composition can have a more ideal combination of high partition coefficient for the extraction of butanol and low toxicity for the butanol-producing microorganism than either the first solvent or second solvent alone.

With regard to a high partition coefficient, it was determined that solvents with hydrogen bonding characteristics and/or high free volume have a high butanol partition coefficient ($K_d$). Increased hydrogen bonding characteristics can be achieved by having a greater number of hydrogen bonding sites per molecule. Free volume in the organic phase can be achieved using solvents whose molecules have a high degree of branching and do not pack closely. In some embodiments, an organic extractant composition with a better mix of both characteristics can be obtained by mixing two or more solvents, one with hydrogen bonding characteristics, and the other with high free volume. In other embodiments, a single solvent can have both hydrogen bonding characteristics and free volume.

Suitable solvents with hydrogen bonding sites that can be used in the organic extractant composition include, but are not limited to, 2-ethyl-1-hexanol, $(R)_3P=O$, wherein each R can independently be hexyl or octyl, tributyl phosphate, bis(2-ethyl hexyl) phosphate, 3,7-dimethyl-1-octanol, 3,5,5-trimethyl-1-hexanol, nonyl phenol, farnesol, oleyl alcohol, 2-butyl-1-octanol, 2-hexyl-1-decanol, castor oil fatty acid methyl ester, soy oil fatty acids (SOFA), bis-(2-ethylhexyl) adipate, corn oil, or corn oil fatty acids (COFA). The solvents can be either hydrogen bond donors (e.g., solvents with alcohol, carboxylic acid or amide functional groups) or hydrogen bond acceptors (e.g., solvents with ester, phosphate, or alkyl amide functional groups). In some embodiments, the first solvent has a higher concentration of hydrogen bonding sites than the second solvent. In such instances, for example, the first solvent can be 3,7-dimethyl-1-octanol and the second solvent can be petroleum ether.

Suitable solvents with relatively high free volume include, but are not limited to, bis(2-ethylhexyl)maleate and 2-butyl-1-octanol.

In some embodiments, the first solvent (having a higher butanol partition coefficient and a higher toxicity level to the microorganism than the second solvent) is 2-ethyl-1-hexanol, $(R)_3P=O$, wherein each R can independently be hexyl or octyl, tributyl phosphate, bis(2-ethyl hexyl) phosphate, 3,7-dimethyl-1-octanol, 3,5,5-trimethyl-1-hexanol, nonyl phenol, farnesol, or mixtures thereof, and the second solvent is oleyl alcohol, 2-butyl-1-octanol, 2-hexyl-1-decanol, castor oil fatty acid methyl ester, soy oil fatty acids, bis-(2-ethylhexyl) adipate, petroleum ether, corn oil, corn oil fatty acids (COFA), or mixtures thereof. In some embodiments, the first solvent is 2-ethyl-1-hexanol, tributyl phosphate, or (R)3P=O, wherein each R may independently be hexyl or octyl, and the second solvent is oleyl alcohol. In some embodiments, the first solvent is 2-ethyl-1-hexanol, tributyl phosphate, or (R)3P=O, wherein each R may independently be hexyl or octyl, and the second solvent is sunflower oil fatty acids. In some embodiments, the first solvent is 2-ethyl-1-hexanol, tributyl phosphate, or (R)3P=O, wherein each R may independently be hexyl or octyl, and the second solvent is bis-(2-ethylhexyl) adipate. In some embodiments, the first solvent is 2-ethyl-1-hexanol, tributyl phosphate, or (R)3P=O, wherein each R may independently be hexyl or octyl, and the second solvent is petroleum ether.

In some embodiments, the first solvent has a butanol partition coefficient of at least about 3.5, about 4, about 4.5, about 5, about 5.5, about 6, about 6.5, about 7, about 7.5, or about 8. In some embodiments, the first solvent has a higher concentration of hydrogen bonding sites per molecule than the second solvent. In some embodiments, the first solvent has more free volume than the second solvent.

The relative amounts of the first and second solvents which form the extractant can vary within a suitable range.

In one embodiment, the extractant can contain about 30 percent to about 90 percent of the first solvent, based on the total volume of the first and second solvents. In one embodiment, the extractant can contain about 40 percent to about 80 percent first solvent. In one embodiment, the extractant can contain about 45 percent to about 75 percent first solvent. In another embodiment, the extractant can contain about 50 percent to about 70 percent first solvent. The optimal range reflects maximization of the extractant characteristics, for example balancing a relatively high partition coefficient for butanol with an acceptable level of biocompatibility or toxicity for the microorganism. For a two-phase extractive fermentation for the production or recovery of butanol, the temperature, contacting time, butanol concentration in the fermentation medium, relative amounts of extractant and fermentation medium, specific first and second solvents used, relative amounts of the first and second solvents, presence of other organic solutes, and the amount and type of microorganism are related; thus, these variables can be adjusted as necessary within appropriate limits to optimize the extraction process as described herein.

The first and second solvents can be available commercially from various sources, in various grades, many of which can be suitable for use in extractive fermentation to produce or recover butanol by the methods disclosed herein. Technical grades of a solvent can contain a mixture of compounds, including the desired component and higher and lower molecular weight components or isomers.

Growth for Production

Recombinant host cells disclosed herein are contacted with suitable carbon substrates, typically in fermentation media. Additional carbon substrates may include, but are not limited to, monosaccharides such as fructose, oligosaccharides such as lactose, maltose, galactose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates can include ethanol, lactate, succinate, or glycerol.

Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1 Compd.*, [Int. Symp.], 7$^{th}$ (1993), 415-32, Editors: Murrell, J. Collin, Kelly, Don P.; Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Patent Application Publication No. 2007/0031918 A1, which is herein incorporated by reference. Biomass, when used in reference to carbon substrate, refers to any cellulosic or lignocellulosic material and includes materials comprising cellulose, and optionally further comprising hemicellulose, lignin, starch, oligosaccharides and/or monosaccharides. Biomass can also comprise additional components, such as protein and/or lipid. Biomass can be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of an enzymatic pathway described herein.

Culture Conditions

Typically cells are grown at a temperature in the range of about 20° C. to about 40° C. in an appropriate medium. Suitable growth media in the present invention are common commercially prepared media such as Luria Bertani (LB) broth, Sabouraud Dextrose (SD) broth or Yeast Medium (YM) broth or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media can also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate (cAMP), can also be incorporated into the fermentation medium.

Suitable pH ranges for the fermentation are between pH 5.0 to pH 9.0, where pH 6.0 to pH 8.0 is preferred for the initial condition. Suitable pH ranges for the fermentation of yeast are typically between about pH 3.0 to about pH 9.0. In one embodiment, about pH 5.0 to about pH 8.0 is used for the initial condition. Suitable pH ranges for the fermentation of other microorganisms are between about pH 3.0 to about pH 7.5. In one embodiment, about pH 4.5 to about pH 6.5 is used for the initial condition.

Fermentations can be performed under aerobic or anaerobic conditions. In one embodiment, anaerobic or microaerobic conditions are used for fermentation.

Industrial Batch and Continuous Fermentations

Butanol, or other products, can be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples can be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Butanol, or other products, may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol, or other products, can be practiced using batch, fed-batch or continuous processes and that any known mode of fermentation would be suitable. Additionally, it is contemplated that cells can be immobilized on a substrate as whole cell catalysts and subjected to fermentation conditions for butanol production.

Methods for Recovering Butanol Using Two-Phase Extractive Fermentation

Bioproduced butanol may be recovered from a fermentation medium containing butanol, water, at least one fermentable carbon source, and a microorganism that has been genetically modified (that is, genetically engineered) to produce butanol via a biosynthetic pathway from at least one carbon source. The first step in the process is contacting the fermentation medium with a water immiscible organic extractant composition comprising a solvent, as described above, to form a two-phase mixture comprising an aqueous phase and a butanol-containing organic phase. "Contacting" means the fermentation medium and the organic extractant composition or its solvent component(s) are brought into physical contact at any time during the fermentation process. In one embodiment, the fermentation medium further comprises ethanol, and the butanol-containing organic phase can contain ethanol.

In certain embodiments where more than one solvent is used for the extraction, the contacting may be performed with the solvents of the extractant composition having been previously combined. For example, the first and second solvents may be combined in a vessel such as a mixing tank to form the extractant, which is then added to a vessel containing the fermentation medium. Alternatively, the contacting may be performed with the first and second solvents becoming combined during the contacting. For example, the first and second solvents may be added separately to a vessel which contains the fermentation medium. In one embodiment, contacting the fermentation medium with the organic extractant composition further comprises contacting the fermentation medium with the first solvent prior to contacting the fermentation medium and the first solvent with the second solvent. In one embodiment, the contacting with the second solvent occurs in the same vessel as the contacting with the first solvent. In one embodiment, the contacting with the second solvent occurs in a different vessel from the contacting with the first solvent. For example, the first solvent may be contacted with the fermentation medium in one vessel, and the contents transferred to another vessel in which contacting with the second solvent occurs.

The organic extractant composition can contact the fermentation medium at the start of the fermentation forming a biphasic fermentation medium. Alternatively, the organic extractant composition can contact the fermentation medium after the microorganism has achieved a desired amount of growth, which can be determined by measuring the optical density of the culture.

Further, the organic extractant composition can contact the fermentation medium at a time at which the butanol level in the fermentation medium reaches a preselected level, for example, before the butanol concentration reaches a toxic level. The butanol concentration can be monitored during the fermentation using methods known in the art, such as gas chromatography or high performance liquid chromatography.

Fermentation can be run under aerobic conditions for a time sufficient for the culture to achieve a preselected level of growth, as determined by optical density measurement. An inducer can then be added to induce the expression of the butanol biosynthetic pathway in the modified microorganism, and fermentation conditions are switched to microaerobic or anaerobic conditions to stimulate butanol production, as described, for example, in detail in Example 6 of US Patent Application Publication No. 2009/0305370. The extractant is added after the switch to microaerobic or anaerobic conditions.

Through contacting the fermentation medium with the organic extractant composition, the butanol product partitions into the organic extractant, decreasing the concentration in the aqueous phase containing the microorganism, thereby limiting the exposure of the production microorganism to the inhibitory butanol product. The volume of the organic extractant to be used depends on a number of factors, including the volume of the fermentation medium, the size of the fermentor, the partition coefficient of the extractant for the butanol product, and the fermentation mode chosen, as described below. The volume of the organic extractant is about 3% to about 60% of the fermentor working volume. The ratio of the extractant to the fermentation medium is from about 1:20 to about 20:1 on a volume:volume basis, for example from about 1:15 to about 15:1, or from about 1:12 to about 12:1, or from about 1:10 to about 10:1, or from about 1:9 to about 9:1, or from about 1:8 to about 8:1.

The next step is separating the butanol-containing organic phase from the aqueous phase using methods known in the art, including but not limited to, siphoning, decantation, centrifugation, using a gravity settler, and membrane-assisted phase splitting. Recovery of the butanol from the butanol-containing organic phase can be done using methods known in the art, including but not limited to, distillation, adsorption by resins, separation by molecular sieves, and pervaporation. Specifically, distillation can be used to recover the butanol from the butanol-containing organic phase.

Gas stripping can be used concurrently with the solvents of the organic extractant composition to remove the butanol product from the fermentation medium. Gas stripping may be done by passing a gas such as air, nitrogen, or carbon dioxide through the fermentation medium, thereby forming a butanol-containing gas phase. The butanol product may be recovered from the butanol-containing gas phase using methods known in the art, such as using a chilled water trap to condense the butanol, or scrubbing the gas phase with a solvent.

Any butanol remaining in the fermentation medium after the fermentation run is completed may be recovered by continued extraction using fresh or recycled organic extractant. Alternatively, the butanol can be recovered from the fermentation medium using methods known in the art, including, but not limited to distillation, azeotropic distillation, liquid-liquid extraction, adsorption, gas stripping, membrane evaporation, pervaporation, and the like.

The two-phase extractive fermentation method may be carried out in a continuous mode in a stirred tank fermentor. In this mode, the mixture of the fermentation medium and the butanol-containing organic extractant composition is removed from the fermentor. The two phases are separated by means known in the art including, but not limited to, siphoning, decantation, centrifugation, using a gravity settler, membrane-assisted phase splitting, and the like, as described above. After separation, the fermentation medium may be recycled to the fermentor or may be replaced with fresh medium. Then, the extractant is treated to recover the butanol product as described above. The extractant may then be recycled back into the fermentor for further extraction of the product. Alternatively, fresh extractant may be continuously added to the fermentor to replace the removed extractant. This continuous mode of operation offers several advantages. Because the product is continually removed from the reactor, a smaller volume of organic extractant composition is required enabling a larger volume of the fermentation medium to be used. This results in higher production yields. The volume of the organic extractant composition may be about 3% to about 50% of the fermentor working volume; 3% to about 20% of the fermentor working volume; or 3% to about 10% of the fermentor working volume. It is beneficial to use the smallest amount of extractant in the fermentor as possible to maximize the volume of the aqueous phase, and therefore, the amount of cells in the fermentor. The process may be operated in an entirely continuous mode in which the extractant is continuously recycled between the fermentor and a separation apparatus and the fermentation medium is continuously removed from the fermentor and replenished with fresh medium. In this entirely continuous mode, the butanol product is not allowed to reach the critical toxic concentration and fresh nutrients are continuously provided so that the fermentation may be carried out for long periods of time. The apparatus that may be used to carry out these modes of two-phase extractive fermentations are well known in the art. Examples are described, for example, by Kollerup et al. in U.S. Pat. No. 4,865,973.

Batchwise fermentation mode may also be used. Batch fermentation, which is well known in the art, is a closed system in which the composition of the fermentation medium is set at the beginning of the fermentation and is not subjected to artificial alterations during the process. In this mode, a volume of organic extractant composition is added to the fermentor and the extractant is not removed during the process. The organic extractant composition may be formed in the fermentor by separate addition of the first and the second solvents, or the solvents may be combined to form the extractant composition prior to the addition of the extractant composition to the fermentor. Although this mode is simpler than the continuous or the entirely continuous modes described above, it requires a larger volume of organic extractant composition to minimize the concentration of the inhibitory butanol product in the fermentation medium. Consequently, the volume of the fermentation medium is less and the amount of product produced is less than that obtained using the continuous mode. The volume of the organic extractant composition in the batchwise mode may be 20% to about 60% of the fermentor working volume; or 30% to about 60% of the fermentor working volume. It is beneficial to use the smallest volume of extractant in the fermentor as possible, for the reason described above.

Fed-batch fermentation mode may also be used. Fed-batch fermentation is a variation of the standard batch system, in which the nutrients, for example glucose, are added in increments during the fermentation. The amount and the rate of addition of the nutrient may be determined by routine experimentation. For example, the concentration of critical nutrients in the fermentation medium may be monitored during the fermentation. Alternatively, more easily measured factors such as pH, dissolved oxygen, and the partial pressure of waste gases, such as carbon dioxide, may be monitored. From these measured parameters, the rate of nutrient addition may be determined. The amount of organic extractant composition used and its methods of addition in this mode is the same as that used in the batchwise mode, described above.

Extraction of the product may be done downstream of the fermentor, rather than in situ. In this external mode, the extraction of the butanol product into the organic extractant composition is carried out on the fermentation medium removed from the fermentor. The amount of organic solvent used is about 20% to about 60% of the fermentor working volume; or 30% to about 60% of the fermentor working volume. The fermentation medium may be removed from the fermentor continuously or periodically, and the extraction of the butanol product by the organic extractant composition may be done with or without the removal of the cells from the fermentation medium. The cells may be removed from the fermentation medium by means known in the art including, but not limited to, filtration or centrifugation. After separation of the fermentation medium from the extractant by means described above, the fermentation medium may be recycled into the fermentor, discarded, or treated for the removal of any remaining butanol product. Similarly, the isolated cells may also be recycled into the fermentor. After treatment to recover the butanol product, the extractant, the first solvent, and/or the second solvent may be recycled for use in the extraction process. Alternatively, fresh extractant may be used. In this mode the extractant is not present in the fermentor, so the toxicity of the extractant is much less of a problem. If the cells are separated from the fermentation medium before contacting with the extractant, the problem of extractant toxicity is further reduced. Furthermore, using this external mode there is less chance of forming an emulsion and evaporation of the extractant is minimized, alleviating environmental concerns.

An improved method for the production of butanol is provided, wherein a microorganism that has been genetically modified of being capable of converting at least one fermentable carbon source into butanol, is grown in a biphasic fermentation medium. The biphasic fermentation medium comprises an aqueous phase and a water immiscible organic extractant composition, as described above, wherein the biphasic fermentation medium comprises from about 3% to about 60% by volume of the organic extractant. The microorganism can be grown in the biphasic fermentation medium for a time sufficient to extract butanol into the extractant composition to form a butanol-containing organic phase. In the case where the fermentation medium further comprises ethanol, the butanol-containing organic phase can contain ethanol. The butanol-containing organic phase is then separated from the aqueous phase, as described above. Subsequently, the butanol is recovered from the butanol-containing organic phase, as described above.

Also provided is an improved method for the production of butanol wherein a microorganism that has been genetically modified to produce butanol via a biosynthetic pathway from at least one carbon source, is grown in a fermentation medium wherein the microorganism produces the butanol into the fermentation medium to produce a butanol-containing fermentation medium. At least a portion of the butanol-containing fermentation medium is contacted with a water immiscible organic extractant composition, as defined herein, to form a two-phase mixture comprising an aqueous phase and a butanol-containing organic phase. In some embodiments, the fermentation medium further comprises ethanol, and the butanol-containing organic phase can contain ethanol. The butanol-containing organic phase is then separated from the aqueous phase, as described above. Subsequently, the butanol is recovered from the butanol-containing organic phase, as described above. At least a portion of the aqueous phase is returned to the fermentation medium.

Isobutanol can be produced by extractive fermentation with the use of a modified *Escherichia coli* strain in combination with an oleyl alcohol as the organic extractant, as disclosed, for example, in US Patent Application Publication No. 2009/0305370. The method yields a higher effective titer for isobutanol (i.e., 37 g/L) compared to using conventional fermentation techniques (see Example 6 of US Patent Application Publication No. 2009/0305370). For example, Atsumi et al. (Nature 451(3):86-90, 2008) report isobutanol titers up to 22 g/L using fermentation with an *Escherichia coli* that was genetically modified to contain an isobutanol biosynthetic pathway. The higher butanol titer obtained with the extractive fermentation method disclosed in US Patent Application Publication No. 2009/0305370 results, in part, from the removal of the toxic butanol product from the fermentation medium, thereby keeping the level below that which is toxic to the microorganism. It is reasonable to assume that the present extractive fermentation method employing a water-immiscible organic extractant composition, as defined herein, would be used in a similar way and provide similar results.

Butanol produced by the method disclosed herein can have an effective titer of greater than about 20 g per liter of the fermentation medium, greater than about 22 g per liter of the fermentation medium, greater than about 25 g per liter of the fermentation medium, greater than about 30 g per liter of the fermentation medium, greater than about 35 g per liter of the fermentation medium, greater than about 37 g per liter of the fermentation medium, greater than about 40 g per liter of the fermentation medium, greater than about 45 g per liter of the fermentation medium, greater than about 50 g per liter of the fermentation medium. In some embodiments, the recovered butanol has an effective titer from about 22 g per liter to about 50 g per liter, about 22 g per liter to 40 g per liter, about 22 g per liter to about 30 g per liter, about 25 g per liter to about 50 g per liter, about 25 g per liter to 40 g per liter, about 25 g per liter to about 30 g per liter, about 30 g per liter to about 50 g per liter, about 40 g per liter to about 50 g per liter, about 22 g per liter to about 60 g per liter, about 30 g per liter to about 60 g per liter, about 40 g per liter to about 60 g per liter, about 22 g per liter to about 80 g per liter, about 40 g per liter to about 80 g per liter, about 50 g per liter to about 80 g per liter, about 65 g per liter to about 80 g per liter.

The present methods are generally described below with reference to a FIG. 1 through FIG. 7.

Referring now to FIG. 1, there is shown a schematic representation of one embodiment of processes for producing and recovering butanol using in situ extractive fermentation. An aqueous stream 10 of at least one fermentable carbon source is introduced into a fermentor 20, which contains at least one recombinant microorganism (not shown) capable of converting the at least one fermentable carbon source into butanol. A stream of a first solvent 12 and a stream of an optional second solvent 14 are introduced to a vessel 16, in which the solvents are combined to form the extractant 18. A stream of the extractant 18 is introduced into the fermentor 20, in which contacting of the fermentation medium with the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Figure 2:
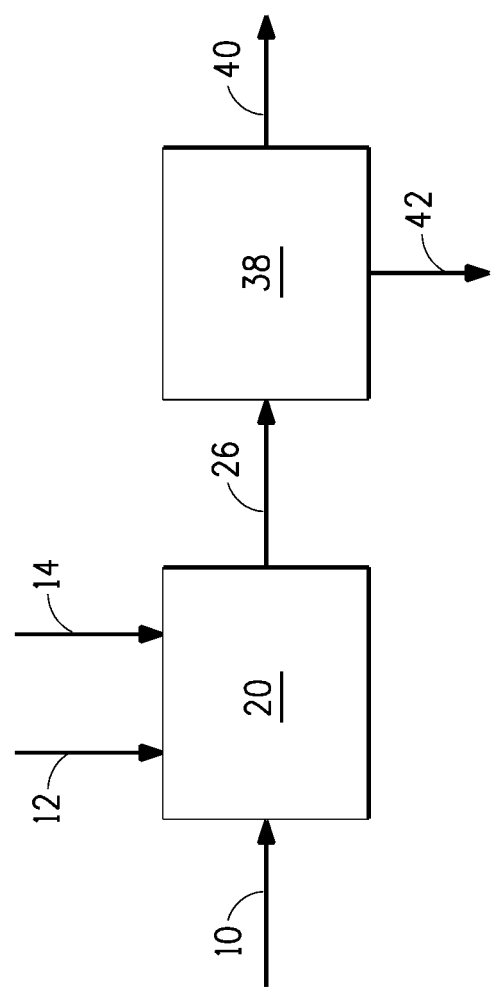
FIG. 2 schematically illustrates one embodiment of the methods of the invention, in which the first solvent and the second solvent of which the extractant composition is comprised are added separately to a fermentation vessel in which the fermentation medium is contacted with the extractant.

Referring now to FIG. 2, there is shown a schematic representation of one embodiment of processes for producing and recovering butanol using in situ extractive fermentation. An aqueous stream 10 of at least one fermentable carbon source is introduced into a fermentor 20, which contains at least one recombinant microorganism (not shown) capable of converting the at least one fermentable carbon source into butanol. A stream of the first solvent 12 and a stream of the optional second solvent 14 of which the extractant is comprised are introduced separately to the fermentor 20, in which contacting of the fermentation medium with the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Figure 3:
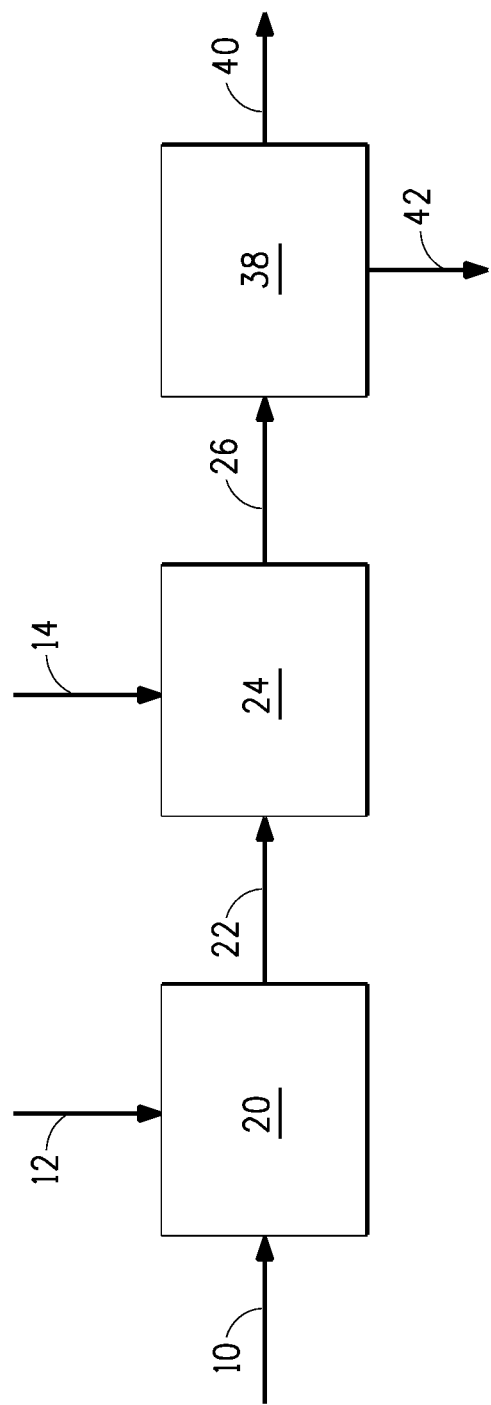
FIG. 3 schematically illustrates one embodiment of the methods of the invention, in which the first solvent and the second solvent of which the extractant composition is comprised are added separately to different fermentation vessels for contacting of the fermentation medium with the extractant.

Referring now to FIG. 3, there is shown a schematic representation of one embodiment of processes for producing and recovering butanol using in situ extractive fermentation. An aqueous stream 10 of at least one fermentable carbon source is introduced into a first fermentor 20, which contains at least one recombinant microorganism (not shown) capable of converting the at least one fermentable carbon source into butanol. A stream of the first solvent 12 of which the extractant is comprised is introduced to the fermentor 20, and a stream 22 comprising a mixture of the first solvent and the contents of fermentor 20 is introduced into a second fermentor 24. A stream of the optional second solvent 14 of which the extractant is comprised is introduced into the second fermentor 24, in which contacting of the fermentation medium with the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Figure 4:
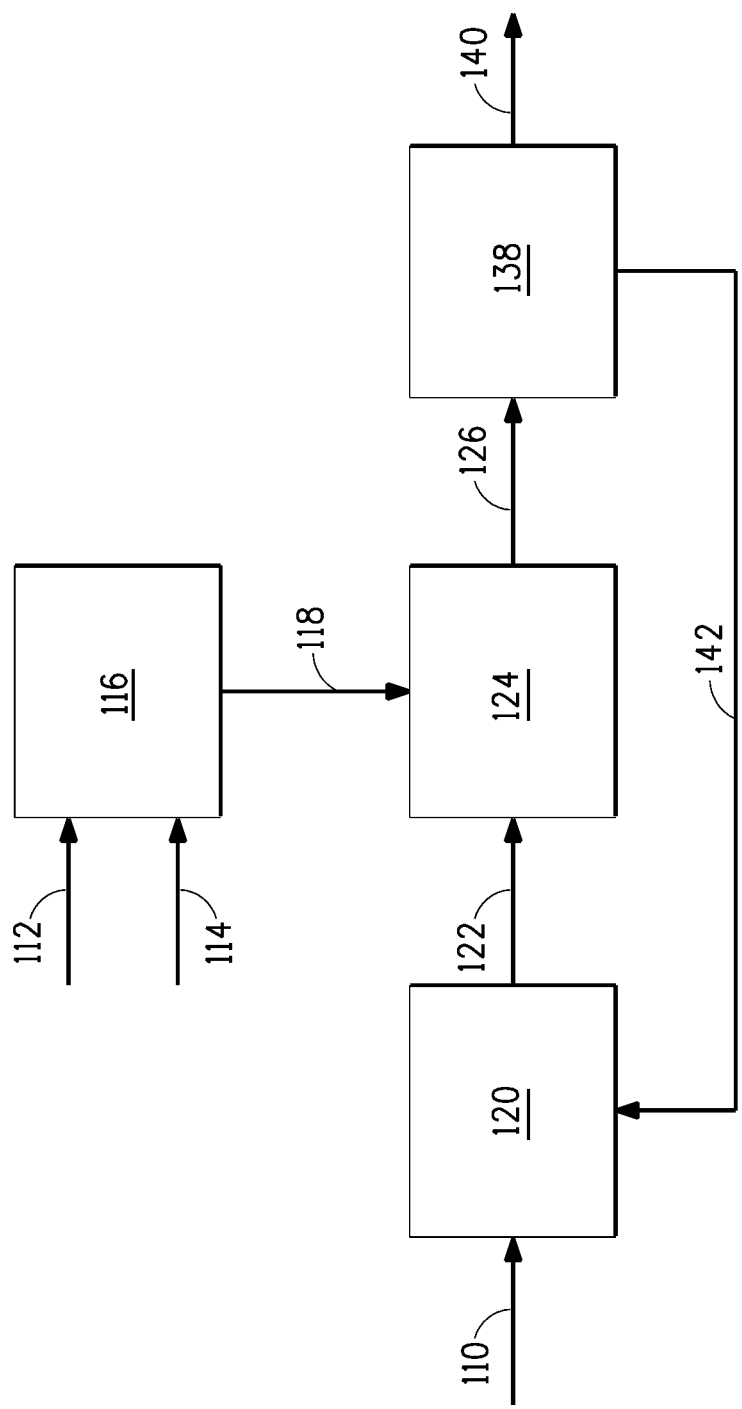
FIG. 4 schematically illustrates one embodiment of the methods of the invention, in which extraction of the product occurs downstream of the fermentor and the first solvent and the second solvent of which the extractant composition is comprised are combined in a vessel prior to contacting the fermentation medium with the extractant in a different vessel.

Referring now to FIG. 4, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one recombinant microorganism (not shown) capable of converting the at least one fermentable carbon source into butanol. A stream of the first solvent 112 and a stream of the optional second solvent 114 are introduced to a vessel 116, in which the solvents are combined to form the extractant 118. At least a portion, shown as stream 122, of the fermentation medium in fermentor 120 is introduced into vessel 124. A stream of the extractant 118 is also introduced into vessel 124, in which contacting of the fermentation medium with the extractant to form a two-phase mixture comprising an aqueous phase and a butanol-containing organic phase occurs. A stream 126 comprising both the aqueous and organic phases is introduced into a vessel 138, in which separation of the aqueous and organic phases is performed to produce a butanol-containing organic phase 140 and an aqueous phase 142.

Figure 5:
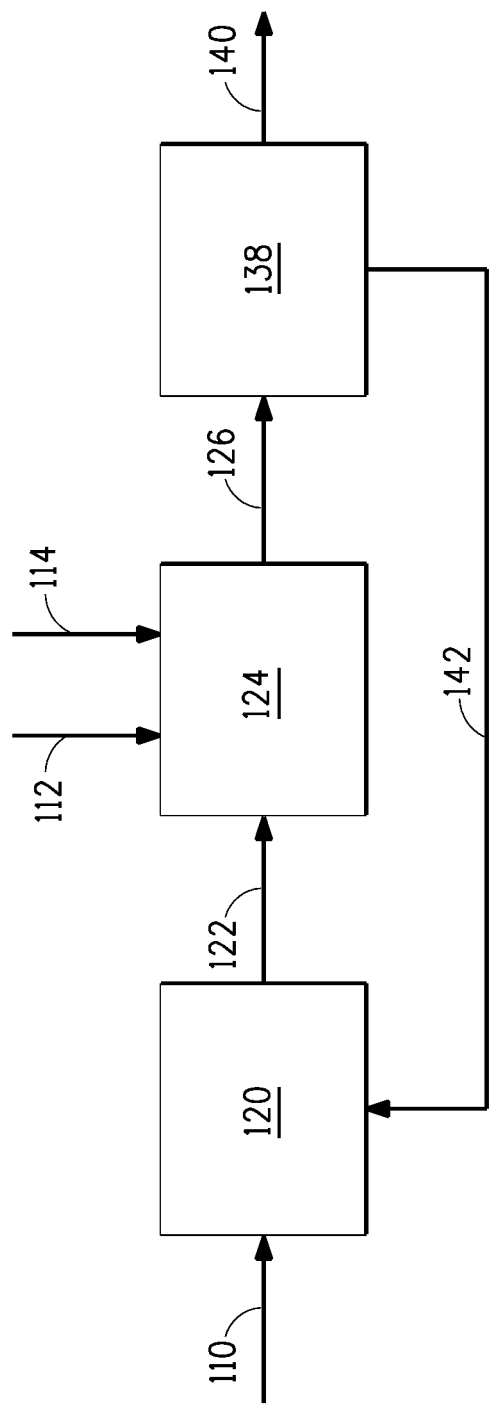
FIG. 5 schematically illustrates one embodiment of the methods of the invention, in which extraction of the product occurs downstream of the fermentor and the first solvent and the second solvent of which the extractant composition is comprised are added separately to a vessel in which the fermentation medium is contacted with the extractant.

Referring now to FIG. 5, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one recombinant microorganism (not shown) capable of converting the at least one fermentable carbon source into butanol. A stream of the first solvent 112 and a stream of the optional second solvent 114 of which the extractant is comprised are introduced separately to a vessel 124, in which the solvents are combined to form the extractant 118. At least a portion, shown as stream 122, of the fermentation medium in fermentor 120 is also introduced into vessel 124, in which contacting of the fermentation medium with the extractant to form a two-phase mixture comprising an aqueous phase and a butanol-containing organic phase occurs. A stream 126 comprising both the aqueous and organic phases is introduced into a vessel 138, in which separation of the aqueous and organic phases is performed to produce a butanol-containing organic phase 140 and an aqueous phase 142.

Figure 6:
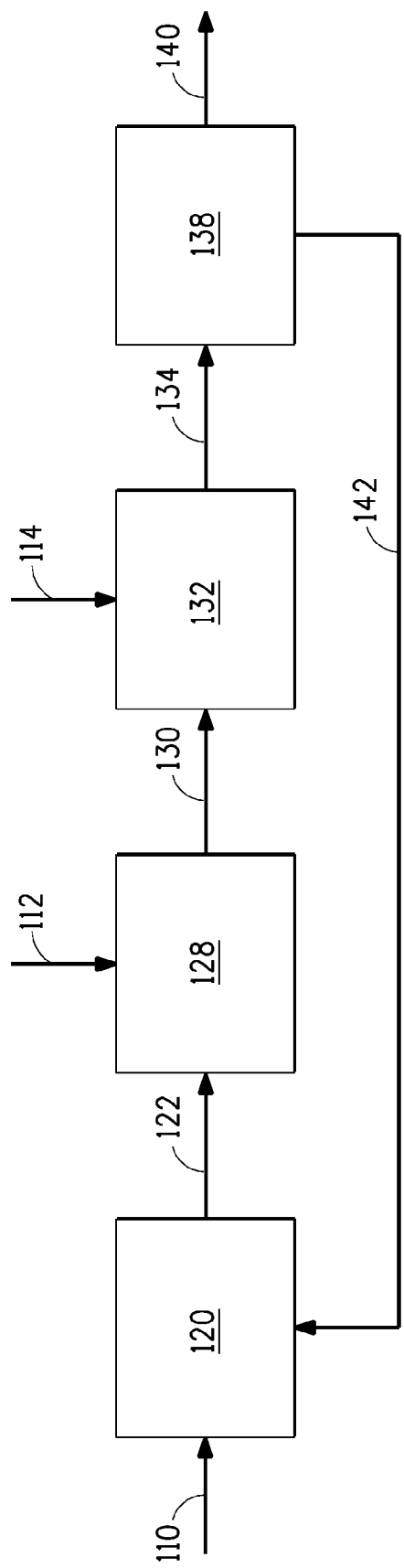
FIG. 6 schematically illustrates one embodiment of the methods of the invention, in which extraction of the product occurs downstream of the fermentor and the first solvent and the second solvent of which the extractant composition is comprised are added separately to different vessels for contacting of the fermentation medium with the extractant.

Referring now to FIG. 6, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one recombinant microorganism (not shown) capable of converting the at least one fermentable carbon source into butanol. A stream of the first solvent 112 of which the extractant is comprised is introduced to a vessel 128, and at least a portion, shown as stream 122, of the fermentation medium in fermentor 120 is also introduced into vessel 128. A stream 130 comprising a mixture of the first solvent and the contents of fermentor 120 is introduced into a second vessel 132. A stream of the optional second solvent 114 of which the extractant is comprised is introduced into the second vessel 132, in which contacting of the fermentation medium with the extractant to form a two-phase mixture comprising an aqueous phase and a butanol-containing organic phase occurs. A stream 134 comprising both the aqueous and organic phases is introduced into a vessel 138, in which separation of the aqueous and organic phases is performed to produce a butanol-containing organic phase 140 and an aqueous phase 142.

The extractive processes described herein can be run as batch processes or can be run in a continuous mode where fresh extractant is added and used extractant is pumped out such that the amount of extractant in the fermentor remains constant during the entire fermentation process. Such continuous extraction of products and byproducts from the fermentation can increase effective rate, titer and yield.

Figure 7:
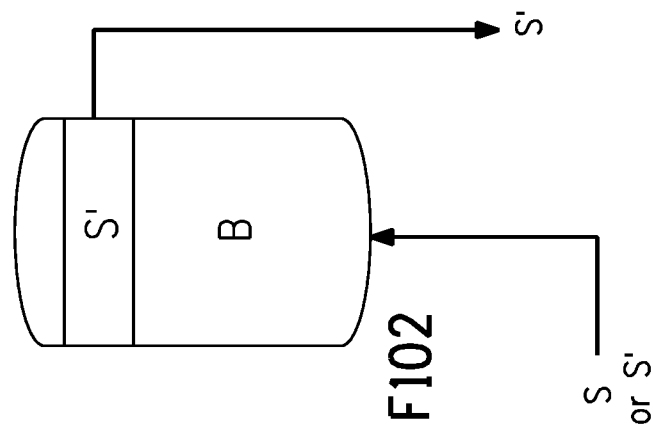
FIG. 7 schematically illustrates one embodiment of the methods of the invention, in which extraction of the product occurs in at least one batch fermentor via co-current flow of a water-immiscible extractant comprising a first solvent and a second solvent at or near the bottom of a fermentation mash to fill the fermentor with an extractant composition which flows out of the fermentor at a point at or near the top of the fermentor.
Figure 7:
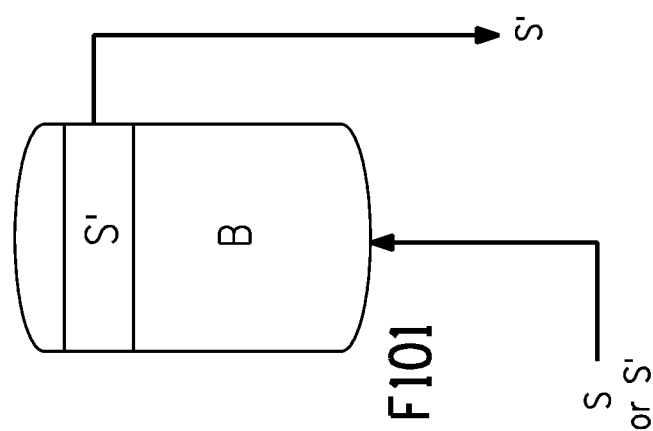
Figure 7:
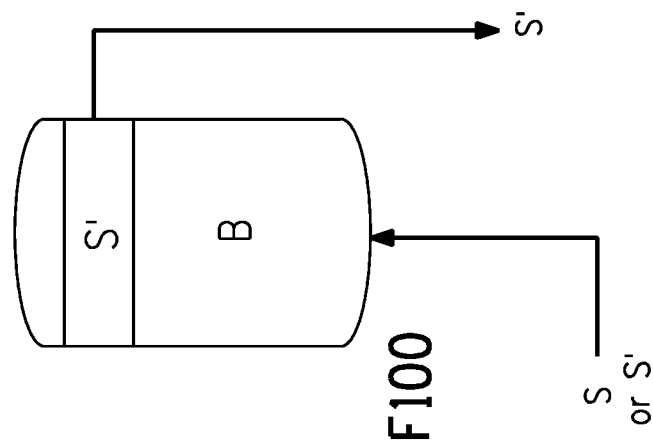

In yet another embodiment, it is also possible to operate the liquid-liquid extraction in a flexible co-current or, alternatively, counter-current way that accounts for the difference in batch operating profiles when a series of batch fermentors are used. In this scenario the fermentors are filled with fermentable mash which provides at least one fermentable carbon source and recombinant microorganism in a continuous fashion one after another for as long as the plant is operating. Referring to FIG. 7, once Fermentor F100 fills with mash and microorganism, the mash and microorganism feeds advance to Fermentor F101 and then to Fermentor F102 and then back to Fermentor F100 in a continuous loop. The fermentation in any one fermentor begins once mash and microorganism are present together and continues until the fermentation is complete. The mash and microorganism fill time equals the number of fermentors divided by the total cycle time (fill, ferment, empty and clean). If the total cycle time is 60 hours and there are 3 fermentors then the fill time is 20 hours. If the total cycle time is 60 hours and there are 4 fermentors then the fill time is 15 hours.

Adaptive co-current extraction follows the fermentation profile assuming the fermentor operating at the higher broth phase titer can utilize the extracting solvent stream richest in butanol concentration and the fermentor operating at the lowest broth phase titer will benefit from the extracting solvent stream leanest in butanol concentration. For example, referring again to FIG. 7, consider the case where Fermentor F100 is at the start of a fermentation and operating at relatively low butanol broth phase (B) titer, Fermentor F101 is in the middle of a fermentation operating at relatively moderate butanol broth phase titer and Fermentor F102 is near the end of a fermentation operating at relatively high butanol broth phase titer. In this case, lean extracting solvent (S), with minimal or no extracted butanol, can be fed to Fermentor F100, the "solvent out" stream (S') from Fermentor F100 having an extracted butanol component can then be fed to Fermentor F101 as its "solvent in" stream and the solvent out stream from F101 can then be fed to Fermentor F102 as its solvent in stream. The solvent out stream from F102 can then be sent to be processed to recover the butanol present in the stream. The processed solvent stream from which most of the butanol is removed can be returned to the system as lean extracting solvent and would be the solvent in feed to Fermentor F100 above.

As the fermentations proceed in an orderly fashion the valves in the extracting solvent manifold can be repositioned to feed the leanest extracting solvent to the fermentor operating at the lowest butanol broth phase titer. For example, assume (a) Fermentor F102 completes its fermentation and has been reloaded and fermentation begins anew, (b) Fermentor F100 is in the middle of its fermentation operating at moderate butanol broth phase titer and (c) Fermentor F101 is near the end of its fermentation operating at relatively higher butanol broth phase titer. In this scenario, the leanest extracting solvent would feed F102, the extracting solvent leaving F102 would feed Fermentor F100 and the extracting solvent leaving Fermentor F100 would feed Fermentor F101.

Advantages of the Present Methods

The present extractive fermentation methods provide butanol known to have an energy content similar to that of gasoline and which can be blended with any fossil fuel. Butanol is favored as a fuel or fuel additive as it yields only $CO_2$ and little or no $SO_x$ or $NO_x$ when burned in the standard internal combustion engine. Additionally, butanol is less corrosive than ethanol, the most preferred fuel additive to date.

In addition to its utility as a biofuel or fuel additive, the butanol produced according to the present methods has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or vehicles. Furthermore, the present methods produce butanol from plant derived carbon sources, avoiding the negative environmental impact associated with standard petrochemical processes for butanol production.

One of the advantages of the present methods is the higher butanol partition coefficient which can be obtained by the appropriate combination of a first and a second solvent as described herein. Extractants having higher partition coefficients can provide more effective extraction of butanol from the fermentation medium. Another advantage of the present method is the ability to use a solvent which has a desirably higher partition coefficient and desirably higher concentration of hydrogen bonding sites but undesirably lower biocompatibility, and to mitigate the lower biocompatibility by the combination with a solvent having higher biocompatibility. As a result, a more effective extractant is obtained, an extractant which can be used in the presence of the microorganism with continued viability of the microorganism.

Further advantages of the present methods include the improved process operability characteristics of the extractant relative to those characteristics of oleyl alcohol. The extractant of the present methods has lower viscosity, lower density, and lower boiling point than oleyl alcohol, which provides improvements to the extraction process using such an extractant. Improved viscosity and density of the extractant can lead to improved efficiency of extraction and ease of phase separation. A lower boiling point can reduce the energy required for distillative separations and can lower the bottoms temperatures in a distillation column separating the butanol from the extractant. Together these characteristics can provide an economic advantage for extractive fermentation using an extractant as disclosed herein.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

Materials

The following materials were used in the examples. All commercial reagents were used as received.

All solvents were obtained from Sigma-Aldrich (St. Louis, Mo.) and were used without further purification. The oleyl alcohol used was technical grade, which contained a mixture of oleyl alcohol (65%) and higher and lower fatty alcohols. The purity of the other solvents used was as follows: 1-nonanol, 98%; 1-decanol, 98%; 1-undecanol, 98%; 2-undecanol, 98%; dodecanol, 98%; 1-nonanal, 98%. Isobutanol (purity 99.5%) was obtained from Sigma-Aldrich and was used without further purification.

Biocompatability Test Method

A preliminary test is performed using an ethanologen (Ethanol Red) because it is a fast growing robust strain that utilizes glucose quickly. If this yeast was found to be biocompatible with the test solvent based on glucose consumption versus a control without solvent, then further testing is carried out using a isobutanologen Ethanologen Test Method:

Seed: Inoculated with 300 uL frozen glycerol stock 250 mL of YPD medium in a baffled 2 L flask. The flask was incubated 16 hours at 30° C./300 rpm to an OD (optical density) of about 10. The seed was diluted in fresh YPD to an OD of about 1.0 then 30 mL were distributed to each 125 mL baffled test flask. At this point, the $OD_{600}$ and glucose g/L was recorded. This will be TO for the entire set.

Next 10 mL of test solvent were added to each flask. Once all components have been added to the flask, the flask was incubated at 30° C./300 rpm. Glucose was monitored over the next 8+ hours by sampling every 4 hours and measuring the glucose concentration of the supernatant. If after 8 hours all glucose has not been consumed, flask was incubated overnight and a final glucose measurement was taken the following day.

Sampling: The flask was pulled from the incubator and allowed to rest for approximately 5 minutes prior to pulling about 1 mL from the aqueous phase (bottom) of the flask placing it in a 1.5 mL centrifuge tube. The sample was centrifuged to ensure most of the solvent had been spun from the aqueous phase and the aqueous phase was analyzed for glucose. Preferred instrument for analysis of glucose was a YSI, but HPLC could be used as well.

Butanologen Test Method:

Plate: Inoculated with a 200 μL frozen glycerol stock on SEG plate by spreading the 200 μL over the entire plate. Incubate 48 hours at 30° C.

Pre-seed: Using an inoculation loop, ⅓ of the plate was harvest and 30 mL of Extractive See Flask Medium was inoculated in a 250 mL baffled flask. The flask was incubated 6 hours at 30° C./300 rpm to an OD of about 5.

Seed: 30 mL were transferred to 300 mL Extractive Seed Flask Medium in a 2 L baffled flask. The flask was incubated 18 hours at 30° C./300 rpm to an OD of about 5. The seed was diluted in fresh Extractive Seed Flask Medium to an OD~1.0. Then 30 mL was distributed to each 125 mL baffled test flask. At this point the $OD_{600}$ and glucose g/L was recorded. This will be TO for the entire set.

10 mL of test solvent was added to each flask. Once all components have been added to the flask, the flask was incubated at 30° C./300 rpm. The glucose was monitored over the next 24+ hours by sampling every 4 hours and glucose concentration of the supernatant was measured.

Sampling: The flask was pulled from the incubator and allowed to rest for approximately 5 minutes prior to sampling about 1 mL from the aqueous phase (bottom) of the flask and placing it in a 1.5 mL centrifuge tube. The sample was centrifuged to ensure most of the solvent had been spun from the aqueous phase and the aqueous phase was analyzed for glucose. The preferred instrument for analysis of glucose was a YSI, but HPLC could be used as well.

Isobutanol Partition Coefficient Test Method 1

The purpose of this method was to determine the approximate partition coefficient of isobutanol between the trial solvent and either water or a salt solution selected to approximate the ion content expected in a cane fermentation. Only one concentration of isobutanol was tested in this method. This method was developed for rapid screening of a number of solvents.

Solutions of isobutanol were made at a 6% level in water and in a salt solution. Half a milliliter of solution and solvent were mixed for an hour, the mixture was centrifuged, and the isobutanol content of the two phases were determined by GC analysis.

Solutions were prepared as follows: to prepare broth solution with 6% isobutanol, 800 g of water were put in a flask and 4.0 g Potassium Chloride, 1.0 g Magnesium Sulphate, 1.0 g calcium sulphate, 0.2 g sodium chloride, and 60 g isobutanol were added. The solution was made up to 1 liter with water. To prepare 6% isobutanol solution, take 800 g of water and add 60 g of isobutanol, and bring up to 1 liter with water.

GC Method

GC analysis was done using a Hewlett Packard 6890 GC using a 30 m FFAP column. Samples were dissolved in isopropanol and 1-pentanol was added as an internal standard. A standard curve was made for isobutanol. Wt % was reported Test Method For each solvent to test: 0.5 ml of Broth Solution with 6% Isobutanol and 0.5 ml of solvent to a 1.5 ml was added to a centrifuge tube. 0.5 ml of 6% Isobutanol Solution and 0.5 ml of solvent was added to a 1.5 ml centrifuge tube. Both tubes were rotated on a vertical rotating platform for one hour at approx. 50 rpm. Both tubes were centrifuged in a centrifuge at 10,000 rpm for 15 minutes (approx. 10,000×g). The layers were separated and the samples were prepared for GC analysis.

Reporting

Wt % of isobutanol in each layer was reported. The density of the pure solvent was also reported. From this data w/v % was calculated by: w/v %=w/w %× density of pure solvent. Wt. iBuOH (mg) was calculated by wt % i-BuOH× 0.5×density of pure solvent. For the aqueous solutions the density of both the pure water and salt solutions were assumed to be 1.0 g/ml. $K_d$ was calculated both from concentration of i-BuOH in the organic/concentration of i-BuOH in the aqueous layer. It was calculated both from the w/w data and w/v data. The sum of the amounts of isobutanol found in both layers was calculated as a check on the data.

Isobutanol Partition Coefficient Test Method 2

For Partition Coefficient Test Method 2, the preparation of solutions and the GC method are identical to Test Method 1.

Test Method

For each solvent to test: 10 ml of Broth Solution with 6% Isobutanol and 1.0 ml of solvent were added to a 15 ml centrifuge tube. 10 ml of 6% Isobutanol Solution and 1.0 ml of solvent were added to a second 15 ml centrifuge tube. Both tubes were rotated on a vertical rotating platform for one hour at approx. 50 rpm. Both tubes were centrifuged at 3000 rpm for 15 minutes. The layers were separated and samples were prepared for GC.

Reporting

Wt % of isobutanol in each layer was reported. The density of the pure solvent was also reported. From this data w/v %, was calculated by: w/v %=w/w %× density of pure solvent. Wt. iBuOH (mg) was calculated by wt % i-BuOH× 0.5×density of pure solvent. For the aqueous solutions the density of both the pure water and salt solutions were assumed to be 1.0 g/ml. $K_d$ was calculated both from concentration of i-BuOH in the organic/concentration of i-BuOH in the aqueous layer. It was calculated both from the w/w data and w/v data. The sum of the amounts of isobutanol found in both layers was calculated as a check on the data.

Example 1

Determination of $K_d$ Values

A number of solvents were tested in an initial screen in order to determine their partition coefficients, using the test methods described above. Table 1 presents the results of the screening technique.

TABLE 1

Partition coefficient data; Determined by Isobutanol Partition Coefficient Test Method 1

| Solvent | density | Water | | Salt solution | |
|---|---|---|---|---|---|
| | | Kd (w/v %) | Kd (w/w %) | Kd (w/v %) | Kd (w/w %) |
| 2-butyl-1-octanol | 0.833 | 3.25 | 3.90 | 3.25 | 3.90 |
| Dioctyl phthlate | 0.985 | 1.27 | 1.29 | 1.33 | 1.35 |
| Bis(2-ethyl hexyl) maleate | 0.944 | 1.40 | 1.48 | 1.48 | 1.57 |
| Bis(2-ethyl hexyl) phosphate | 0.965 | 3.50 | 3.63 | 3.47 | 3.59 |
| Bis(2-ethyl hexyl) phosphate | 0.965 | 3.25 | 3.37 | 3.43 | 3.55 |
| 3,7-dimethyl-1-octanol | 0.828 | 4.37 | 5.28 | 4.21 | 5.08 |
| tributyl phosphate | 0.979 | 5.44 | 5.56 | 5.52 | 5.64 |
| hexyl salicylate | 1.04 | 1.26 | 1.22 | 1.28 | 1.23 |
| butyl dodecanoate | 0.855 | 1.35 | 1.58 | 1.34 | 1.57 |
| propylene carbonate | 1.2 | 0.68 | 0.57 | 0.65 | 0.55 |
| 2-Ethyl-1-hexanol | 0.833 | 4.63 | 5.56 | 5.20 | 6.24 |
| 3,5,5-trimethyl-1-hexanol | 0.824 | 3.98 | 4.83 | 4.40 | 5.35 |
| dioctyl terephthalate | 0.986 | 1.02 | 1.03 | 1.08 | 1.09 |
| bis(2-ethylhexyl)adipate | 0.925 | 1.48 | 1.60 | 1.62 | 1.75 |
| bis(2-ethylhexyl)sebacate | 0.914 | 1.31 | 1.43 | 1.42 | 1.55 |
| nonyl phenol | 0.937 | 6.65 | 7.10 | 6.57 | 7.01 |
| DBE (Dimethyl esters of succinic acid, glutaric acid and adipic acid) | 1.09 | 0.38 | 0.35 | 0.37 | 0.34 |
| FABE (Corn oil fatty acid isobutyl ester) | 0.86 | 1.15 | 1.34 | 1.19 | 1.38 |
| FAEE (Corn oil fatty acid ethyl ester) | 0.87 | 1.40 | 1.60 | 1.47 | 1.69 |
| FAME (corn oil fatty acid methyl ester) | 0.88 | 1.38 | 1.57 | 1.53 | 1.74 |
| Farnesol | 0.89 | 3.79 | 4.26 | 3.55 | 3.99 |
| Xylene | 0.879 | 1.09 | 1.24 | 1.09 | 1.24 |
| chlorobutane | 0.886 | 1.31 | 1.48 | 1.34 | 1.51 |
| petroleum ether | 0.64 | 0.73 | 1.15 | 0.76 | 1.19 |
| Castor FAME (Castor oil fatty acid methyl ester) | 0.9125 | 2.85 | 3.12 | 3.01 | 3.30 |
| SOFA (soy oil fatty acid) | 0.88 | 2.62 | 2.97 | 2.62 | 2.98 |
| FAGE (corn oil fatty acid ethylene glycol ester) | 0.9135 | 2.26 | 2.48 | 2.29 | 2.50 |
| Trialkylphosphine oxide (Cyanex 923) | 0.88 | 7.05 | 8.01 | 7.70 | 8.75 |
| 34A (corn oil fatty acid ester of dipropyleneglycolmono-methyl ether) | 0.901 | 1.64 | 1.82 | 1.69 | 1.88 |
| i-Amyl Ether | 0.78 | 1.38 | 1.76 | 1.48 | 1.90 |
| Hexyl Ether | 0.793 | 1.22 | 1.54 | 1.25 | 1.58 |
| Propylene Glycol MW 2000 | 1.005 | 2.80 | 2.79 | 3.34 | 3.33 |
| Oleyl Alcohol 90-95% | 0.849 | 2.95 | 3.47 | 3.04 | 3.58 |
| 2-Butyl-1-octanol (Isofol 12) | 0.833 | 3.85 | 4.62 | 3.92 | 4.71 |
| 2-Hexyl-1-decanol (Isofol 16) | 0.836 | 2.98 | 3.56 | 1.88 | 2.24 |

As observed in Table 1, a number of solvents had $K_d$ values higher than oleyl alcohol.

Example 2

Designing an Organic Extractant with Two or More Solvents

Based on the IQ values of the solvents above, a number of single solvents were evaluated for their biocompatibility. Biocompatibility was determined by measuring glucose uptake in comparison with oleyl alcohol. Results, shown below, indicate that 2-hexyl-1-decanol (isofol-16) had glucose uptake values similar to oleyl alcohol.

TABLE 2

Biocompatibility Test Results for Single Component Extractants (OD at T = 0 was 1.0)

| Extractant | Kd TM 1 (w/w %) | Glucose (g/L) T = 0 | Glucose (g/L) 4.0 hrs | Glucose (g/L) 24.00 hrs |
|---|---|---|---|---|
| oleyl alcohol | 3.47 | 18.1 | 7.8 | 0.0 |
| 2-Hexyl-1-decanol (Isofol-12) | 4.62 | 18.1 | 16.5 | 0.0 |
| 2-Hexyl-1-decanol (Isofol-16) | 3.6 | 18.1 | 7.5 | 0.0 |

TABLE 3

Toxicity Results for Single Component Extractants (OD at T = 0 was 0.61)

| Solvent | Kd TM 1 (w/w %) | Glucose (g/L) T = 0 | Glucose (g/L) 5.00 hrs Run 1/Run 2 | Glucose (g/L) 24.00 hrs Run 1/Run 2 |
|---|---|---|---|---|
| Control | na | 18.8 | 2.2 | 0.0 |
| 2-butyl-1-octanol (Isofol-12) | 4.62 | 18.8 | 19.3/19.4 | 0.0/0.0 |
| Bis(2-ethyl hexyl) phosphate | 3.4 | 18.8 | 20.3/20.6 | 20.0/20.2 |
| 3,7-dimethyl-1-octanol | 5.28 | 18.8 | 19.7/20.0 | 19.9/19.7 |
| tributyl phosphate | 5.56 | 18.8 | 19.8/20.1 | 20.3/20.5 |
| 2-ethyl-1-hexanol | 5.56 | 18.8 | 19.9/20.0 | 19.6/19.6 |
| 3,5,5-trimethyl-1-hexanol | 4.8 | 18.8 | 20.1/20.1 | 20.3/20.2 |
| nonyl phenol | 7.1 | 18.8 | 20.3/20.3 | 20.6/20.0 |
| farnesol | 4.3 | 18.8 | 19.0/19.0 | 0.66/6.65 |

In order to obtain an organic extractant having the ideal blend of hydrogen bonding characteristics and free volume, several solvent mixtures were evaluated for their biocompatibility. Biocompatibility of the solvent mixtures was determined by testing glucose consumption of an ethanologen in the presence of the solvent mixture. Results from biocompatibility testing are detailed below in Tables 4-6.

TABLE 4

Toxicity Results for Mixtures of Oleyl Alcohol and 2-Ethyl Hexanol (OD at T = 0 was 0.61)

| Solvent | Kd TM1 (w/w %) | Glucose (g/L) T = 0 | Glucose (g/L) 5.00 hrs Run 1/Run 2 | Glucose (g/L) 24.00 hrs Run 1/Run 2 |
|---|---|---|---|---|
| Control | na | 18.8 | 2.2/2.2 | 0.0/0.0 |
| oleyl alcohol | 3.47 | 18.8 | 3.4/3.3 | 0.0/0.0 |
| oleyl alcohol + 10% v/v 2-ethyl-1-hexanol | 3.76 | 18.8 | 11.6/11.7 | 0.0/0.0 |

TABLE 4-continued

Toxicity Results for Mixtures of Oleyl Alcohol and 2-Ethyl Hexanol (OD at T = 0 was 0.61)

| Solvent | Kd TM1 (w/w %) | Glucose (g/L) T = 0 | Glucose (g/L) 5.00 hrs Run 1/Run 2 | Glucose (g/L) 24.00 hrs Run 1/Run 2 |
|---|---|---|---|---|
| oleyl alcohol + 20% v/v 2-ethyl-1-hexanol | 3.99 | 18.8 | 14.0/14.0 | 0.6/0.5 |
| oleyl alcohol + 50% v/v 2-ethyl-1-hexanol | 4.87 | 18.8 | 17.5/17.5 | 16.3/15.9 |

TABLE 5

Toxicity Results for Pure Extractants and Mixtures Containing Cyanex 923 (OD at T = 0 was 1.0)

| Solvent | Kd TM 1 (w/w %) | Glucose (g/L) T = 0 | Glucose (g/L) 4.00 hrs Run 1/Run 2 | Glucose (g/L) 24.00 hrs Run 1/Run 2 |
|---|---|---|---|---|
| oleyl alcohol | 3.47 | 18.1 | 7.9/7.7 | 0.0/0.0 |
| Isofol 12 | 4.62 | 18.1 | 16.4/16.6 | 0.0/0.0 |
| Isofol 16 | 3.6 | 18.1 | 7.5/7.4 | 0.0/0.0 |
| Castor Oil FAME | 3.1 | 18.1 | 6.7/6.8 | 0.0/0.0 |
| oleyl alcohol + Cyanex 923 | ND | 18.1 | 10.8/11.1 | 0.0/0.0 |
| Isofol 12 + Cyanex 923 | ND | 18.1 | 10.6/10.3 | 0.0/0.0 |
| Isofol 16 + Cyanex 923 | ND | 18.1 | 11.9/11.3 | 0.0/0.0 |
| Castor Oil FAME + Cyanex 923 | ND | 18.1 | 11.8/11.8 | 0.0/0.0 |

Cyanex 923 is a mixture of trialkyl phosphine oxides, where the alkyl groups are a mixture of hexyl or octyl groups, i.e., $(R)_3P=O$, wherein each R may independently be hexyl or octyl; Isofol 12 is 2-butyl-1-octanol; Isofol-16 is 2-hexyl-1-decanol.

TABLE 6

Toxicity Results for Mixtures Containing Tributyl Phosphate and 2-ethyl Hexanol (OD at T = 0 was 0.6)

| Solvent | Kd | Glucose (g/L) T = 0 | Glucose (g/L) 5.50 hrs Run 1/Run 2 | Glucose (g/L) 24.00 hrs Run 1/Run 2 |
|---|---|---|---|---|
| oleyl alcohol | 3.47 | 17.1 | 0.0/0.0 | 0.0/0.0 |
| oleyl alcohol + 10% tributyl phosphate | 3.7 | 17.1 | 0.0/0.0 | 0.0/0.0 |
| oleyl alcohol + 20% tributyl phosphate | 4.95 | 17.1 | 0.0/0.0 | 0.0/0.0 |
| SOFA | 2.97 | 17.1 | 0.1/0.2 | 0.0/0.0 |
| SOFA + 10% tributyl phophate | 3.14 | 17.1 | 0.0/0.0 | 0.0/0.0 |
| SOFA + 20% tributyl phophate | 3.5 | 17.1 | 0.0/0.0 | 0.0/0.0 |
| bis-(2-ethylhexyl) adipate | 1.6 | 17.1 | 0.0/0.0 | 0.0/0.0 |
| bis-(2-ethylhexyl) adipate + 10% tributyl phophate | 2.38 | 17.1 | 0.0/0.0 | 0.0/0.0 |
| bis-(2-ethylhexyl) adipate + 20% tributyl phophate | 3.01 | 17.1 | 0.6/0.5 | 0.0/0.0 |
| bis-(2-ethylhexyl) adipate + 10% 2-ethyl hexanol | 2.40 | 17.1 | 13.0/12.9 | 0.0/0.0 |
| bis-(2-ethylhexyl) adipate + 20% 2-ethyl hexanol | 2.91 | 17.1 | 14.3/14.2 | 5.3/5.4 |

As seen from the data presented in Tables above, a mixture of bis(2-Ethyl hexyl) adipate with 10% 2-Ethyl hexanol showed no toxicity. Similarly, a mixture of oleyl alcohol with up to the 20% 2-Ethyl hexanol showed no toxicity to yeast. Also, mixtures of oleyl alcohol and SOFA with up to 50% tributyl phosphate levels showed no loss of uptake of glucose with yeast as opposed to the 100% tributyl phosphate which completely inhibited the uptake of glucose.

In addition to the data presented in Tables 4-6 above, Table 7 shows the partition coefficient values for petroleum ether and tributyl phosphate.

TABLE 7

Kd values of petroleum ether/tributyl phosphate combinations

| Substrate | Density | $K_{D\ TM\ 1}$ (w/w %) |
|---|---|---|
| Tributyl phosphate | 0.979 | 5.56 |
| 50/50 tributyl phosphate/pet ether | 0.78 | 6.28 |
| Pet ether | 0.64 | 1.15 |

What is claimed is:

1. A method for recovering butanol from a fermentation medium, the method comprising:
    (a) providing a fermentation medium comprising butanol, water, and a recombinant microorganism comprising a butanol biosynthetic pathway, wherein the recombinant microorganism produces butanol;
    (b) contacting the fermentation medium with a water immiscible organic extractant composition comprising a first solvent comprising a butanol partition coefficient of at least 3, wherein the first solvent is 2-ethyl-1-hexanol, $(R)_3P=O$, wherein each R may independently be hexyl or octyl, tributyl phosphate, bis(2-ethyl hexyl) phosphate, 3,7-dimethyl-1-octanol, 3,5,5-trimethyl-1-hexanol, nonyl phenol, farnesol, or mixtures thereof, and a second solvent comprising a butanol partition coefficient, wherein the second solvent is oleyl alcohol, 2-butyl-1-octanol, 2-hexyl-1-decanol, castor oil fatty acid methyl ester, soy oil fatty acids (SOFA), bis-(2-ethylhexyl) adipate, petroleum ether, corn oil, corn oil fatty acids (COFA), or mixtures thereof, to form a butanol-containing organic phase and an aqueous phase; and
    (c) recovering the butanol from the butanol-containing organic phase, wherein the butanol partition coefficient of the first solvent is higher than the butanol partition coefficient of the second solvent.

2. The method of claim 1, wherein the first solvent has a butanol partition coefficient of at least about 4.

3. The method of claim 1, wherein the first solvent has a higher concentration of hydrogen bonding sites than the second solvent.

4. The method of claim 1, wherein the first solvent is 2-ethyl-1-hexanol, tributyl phosphate, or $(R)_3P=O$, wherein each R may independently be hexyl or octyl, and the second solvent is oleyl alcohol.

5. The method of claim 1, wherein the first solvent is 2-ethyl-1-hexanol, tributyl phosphate, or $(R)_3P=O$, wherein each R may independently be hexyl or octyl, and the second solvent is sunflower oil fatty acids.

6. The method of claim 1, wherein the first solvent is 2-ethyl-1-hexanol, tributyl phosphate, or $(R)_3P=O$, wherein each R may independently be hexyl or octyl, and the second solvent is bis-(2-ethylhexyl) adipate.

7. The method of claim 1, wherein the first solvent is 2-ethyl-1-hexanol, tributyl phosphate, or $(R)_3P=O$, wherein each R may independently be hexyl or octyl, and the second solvent is petroleum ether.

8. The method of claim 1, wherein the contacting of the organic extractant composition with the fermentation medium occurs in the fermentor.

9. The method of claim 1, further comprising: transferring a portion of the fermentation medium from the fermentor to a vessel, wherein the contacting of the organic extractant composition with the fermentation medium occurs in the vessel.

10. The method of claim 1, wherein the contacting comprises contacting the fermentation medium via a co-current or counter-current stream of the organic extractant composition.

11. The method of claim 1, wherein the recovered butanol has an effective titer from about 20 g per liter to about 40 g per liter of the fermentation medium.

12. The method of claim 1, wherein the recovered butanol has an effective titer of at least about 37 g per liter of the fermentation medium.

13. The method of claim 1, wherein the butanol is isobutanol.

14. A composition, comprising butanol in a water immiscible organic extractant composition, wherein said organic extractant composition comprises:
    (a) a first solvent comprising a butanol partition coefficient of at least 3, wherein the first solvent is 2-ethyl-1-hexanol, $(R)_3P=O$, wherein each R may independently be hexyl or octyl, tributyl phosphate, bis(2-ethyl hexyl) phosphate, 3,7-dimethyl-1-octanol, 3,5,5-trimethyl-1-hexanol, nonyl phenol, farnesol, or mixtures thereof; and
    (b) a second solvent comprising a butanol partition coefficient, wherein the second solvent is oleyl alcohol, 2-butyl-1-octanol, 2-hexyl-1-decanol, castor oil fatty acid methyl ester, soy oil fatty acids (SOFA), bis-(2-ethylhexyl) adipate, petroleum ether, corn oil, corn oil fatty acids (COFA), or mixtures thereof,
wherein the butanol partition coefficient of the first solvent is higher than the butanol partition coefficient of the second solvent.

15. The composition of claim 14, wherein the first solvent has a butanol partition coefficient of at least about 4.

16. The composition of claim 14, wherein the first solvent has a higher concentration of hydrogen bonding sites than the second solvent.

17. The composition of claim 14, wherein the first solvent is 2-ethyl-1-hexanol, tributyl phosphate, or $(R)_3P=O$, wherein each R may independently be hexyl or octyl, and the second solvent is oleyl alcohol.

18. The composition of claim 14, wherein the first solvent is 2-ethyl-1-hexanol, tributyl phosphate, or $(R)_3P=O$, wherein each R may independently be hexyl or octyl, and the second solvent is sunflower oil fatty acids.

19. The composition of claim 14, wherein the first solvent is 2-ethyl-1-hexanol, tributyl phosphate, or $(R)_3P=O$, wherein each R may independently be hexyl or octyl, and the second solvent is bis-(2-ethylhexyl) adipate.

20. The composition of claim 14, wherein the first solvent is 2-ethyl-1-hexanol, tributyl phosphate, or $(R)_3P=O$, wherein each R may independently be hexyl or octyl, and the second solvent is petroleum ether.

21. The composition of claim 14, wherein the butanol is isobutanol.

* * * * *